(12) United States Patent
Barr et al.

(10) Patent No.: US 6,784,205 B2
(45) Date of Patent: Aug. 31, 2004

(54) COMPOUNDS THAT MODULATE THE ACTIVITY OF PTP-1B AND TC-PTP

(75) Inventors: Kenneth Barr, San Francisco, CA (US); Bruce Fahr, Foster City, CA (US); Stig Hansen, El Cerrito, CA (US); Christian Wiesmann, Brisbane, CA (US)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 10/374,539

(22) Filed: Feb. 25, 2003

(65) Prior Publication Data

US 2003/0195247 A1 Oct. 16, 2003

Related U.S. Application Data

(60) Provisional application No. 60/361,475, filed on Mar. 1, 2002.

(51) Int. Cl.⁷ .............................................. A61K 31/34
(52) U.S. Cl. ........................................ 514/469; 549/467
(58) Field of Search ........................... 514/469; 549/467

(56) References Cited

PUBLICATIONS

You–Ten, Kong E. et al., "Impaired Bone Marrow Microenvironment and Immune Function in T Cell Protein Tyrosine Phosphatase–deficient Mice", J. Exp. Journ., vol. 186, No. 5, Aug. 1997, pp. 683–693.

Tonks, Nicholas K. et al., "Combinatorial Control of the Specificity of Protein Tyrosine Phosphatases", Current Opinion in Cell Biology 2001, 13:182–195.

*Primary Examiner*—Amelia A. Owens
(74) *Attorney, Agent, or Firm*—Heller, Ehrman, White & McAuliffe LLP

(57) ABSTRACT

The present invention relates to a new and improved method for treating diabetes and or its associated complications by modulating the activity of protein tryosin phosphatase 1B ("PTP-1B"). The inventive compounds modulate the activity PTP-1B by binding to a novel binding site referred herein as the PTP-1B exosite that is distal to the active site of PTP-1B. The present invention also relates to a new and improved method of treating immune system disorders by modulating the activity of T-cell protein tyrosine phosphatase ("TC-PTP"). The inventive compound modulate the activity of TC-PTP by binding to a novel binding site referred herein as the TC-PTP exosite that is distal to the active site of PTP-1B.

24 Claims, 10 Drawing Sheets

|          | 1                                                                      | 50 |
|----------|------------------------------------------------------------------------|----|
| PTP-1B   | MEMEKEFEQI DKSGSWAAIY QDIRHEASDF PCRVAKLPKN KNRNRYRDVS                  |    |
| hTC-ptp  | MPTTIEREFEEL DTQRRWQPLY LEIRNESHDY PHRVAKFPEN RNRNRYRDVS                |    |

|          | 51                                                                     | 100 |
|----------|------------------------------------------------------------------------|-----|
| PTP-1B   | PFDHSRIKLH QEDNDYINAS LIKMEEAQRS YILTQGPLPN TCGHFWEMVW                  |     |
| hTC-ptp  | PYDHSRVKLQ NAENDYINAS LVDIEEAQRS YILTQGPLPN TCCHFWLMVW                  |     |

|          | 101                                                                    | 150 |
|----------|------------------------------------------------------------------------|-----|
| PTP-1B   | EQKSRGVVML NRVMEKGSLK CAQYWPQKEE KEMIFEDTNL KLTLISEDIK                  |     |
| hTC-ptp  | QQKTKAVVML NRIVEKESVK CAQYWP TDD QEMLFKETGF SVKLLSEDVK                  |     |

|          | 151                                                                    | 200 |
|----------|------------------------------------------------------------------------|-----|
| PTP-1B   | SYYTVRQLEL ENLTTQETRE ILHFHYTTWP DFGVPESPAS FLNFLFKVRE                  |     |
| hTC-ptp  | SYYTVHLLQL ENINSGETRT ISHFHYTTWP DFGVPESPAS FLNFLFKVRE                  |     |

|          | 201                                                                    | 250 |
|----------|------------------------------------------------------------------------|-----|
| PTP-1B   | SGSLSPEHGP VVVHCSAGIG RSGTFCLADT CLLLMDKRKD PSSVDIKKVL                  |     |
| hTC-ptp  | SGSLNPDHGP AVIHCSACIC RSGTFSLVDT CLVLMEKGDD         INIKQVL             |     |

|          | 251                                                                    | 298 |
|----------|------------------------------------------------------------------------|-----|
| PTP-1B   | LEMRKFRMGL IQTADQLRFS YLAVIEGAKF IMGDSSVQDQ WKELSHED                    |     |
| hTC-ptp  | LNMRKYRMGL IQTPDQLRFS YMAIIEGAKC IKGDSSIQKR WKELSKED                    |     |

FIGURE 1

```
            1                                                         50
PTP-1B   ..MEMEKEFEQI  DK..SGSWAAIY  QDIRHEASDF  PCRVAKLPKN  KNRNRYRDVS
LAR      PITDLADNIERL  KANDGLXFSQE   YESIDPGQQF  TWENSNLEVN  KPKNRYANVI 51                                                        100
PTP-1B   PFDHSRIKLH   QED....NDYINAS  LIKMEEAQRS   YILTQGPLPN  TCGHFWEMVW
LAR      AYDHSRVILT   SIDGVPGSDYINAN  YIDGYRKQNA   YIATQGPLPE  TMGDFWRMVW 101                                                       150
PTP-1B   EQKSRGVVML   NRVMEKGSLK   CAQYWPQKEE   KEMIFEDTNL   KLTLISEDIK
LAR      EQRTATVVMM   TRLEEKSRVK   CDQYWPARG.   ...TETCGLI   QVTLLDTVEL 151                                                       200
PTP-1B   SYYTVRQLEL   ENLTTQETRE   ILEFHYTTWP   DFGVPESPAS   FLNFLFKVRE
LAR      ATYTVRTFAL   HKSGSSEKRE   LRQFQFMAWP   DHGVPEYPTP   ILAFLRRVKA 201                                                       250
PTP-1B   SGSLSPEHGP   VVVHCSAGIG   RSGTFCLADT   CLLLMDKRKD   PSSVDIKKVL
LAR      CN.PLDAGP    MVVHCSAGVG   RTGCFIVID.   ..AMLERMKH   EKTVDIYGHV 251                                            298
PTP-1B   LEMRKFRMGL   IQTADQLRFS   YLAVIEGAKF   IMGDSSVQDQ   WKELSHED
LAR      TCMRSQRNYM   VQTEDQYVFI   HEALLEAATC   GHTEVPARNL   YAHIQKLG
```

COMPOUNDS THAT MODULATE THE ACTIVITY OF PTP-1B AND TC-PTP

This application claims the benefit of the priority date of an earlier filed provisional patent application serial No. 60/361,475, filed Mar. 1, 2002 (35 USC 119).

BACKGROUND

Diabetes mellitus is a major risk factor for potentially debilitating diseases such as cardiovascular disease and stroke, and is the leading cause of blindness, renal failure and lower limb amputations in adults. Type 2 or noninsulin-dependent diabetes mellitus accounts for over ninety percent of all diabetes cases. Although current treatments for type 2 diabetes result in lower levels of blood sugar, side effects include weight gain, hyperglycemia, edema, and liver toxicity. Obesity, a condition that is often strongly correlated with diabetes further complicates treatment options. In particular, obesity further exacerbates the insulin resistance that is a hallmark of diabetes so that current treatments for diabetes typically lose their efficacy after a few years. As a result, a need exists for new and improved methods for treating diabetes and/or its associated complications.

DESCRIPTION OF THE FIGURES

FIG. 1 is a sequence alignment of the first 298 residues of human PTP-1B (SEQ ID NO. 1) and the first 296 residues of human TC-PTP (hTC-ptp; SEQ ID NO. 2).

FIG. 7 is a sequence alignment of the first 298 residues of human PTP-1B (SEQ ID NO. 1) and the first 297 residues of human LAR (SEQUENCE ID NO. 3).

In FIG. 10, "3892" corresponds to compound 5 and "Ins" corresponds to insulin.

DESCRIPTION OF THE PREFERRED EMBODIMENTS

A. Definitions

Figure 2:
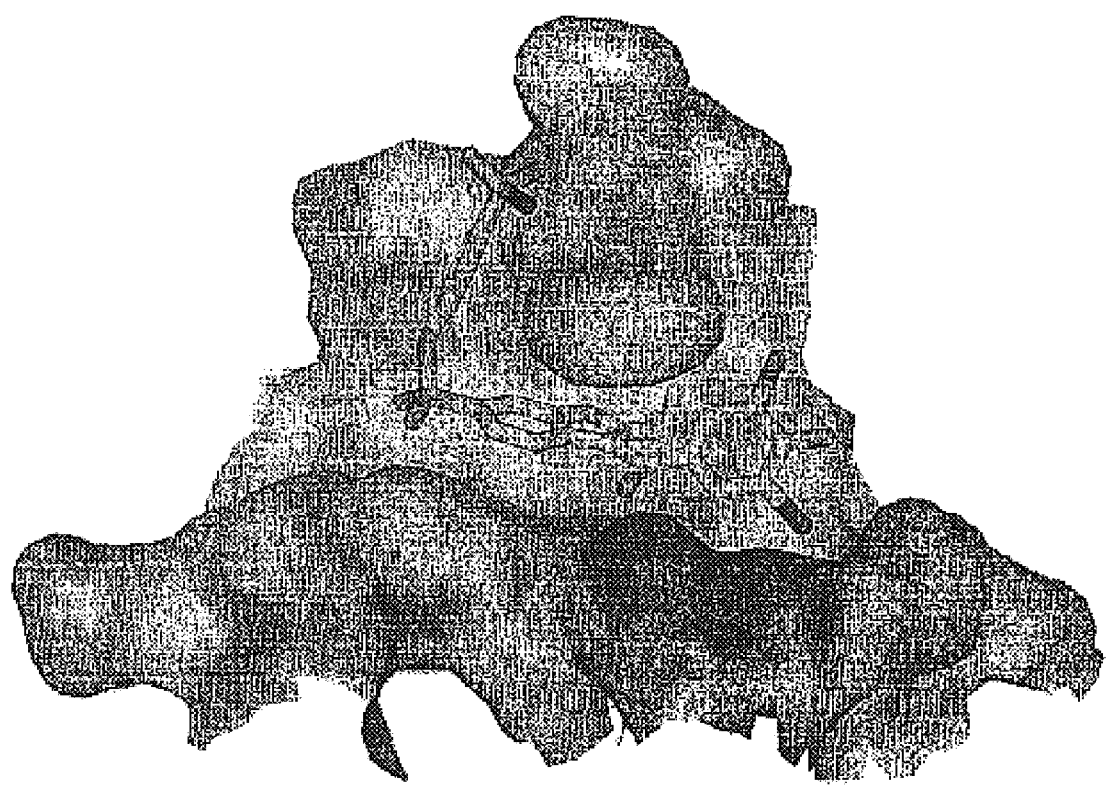
FIG. 2 is the exosite region of PTP-1B complexed with compound 5. The accessible surface of the exosite-forming residues is shown.

Unless defined otherwise, technical and scientific terms used herein have the same meaning as commonly understood by one of ordinary skill in the art to which the invention belongs. References, such as Singleton et al., Dictionary of Microbiology and Molecular Biology 2nd ed., John Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

The terms "type 2 diabetes," "type II diabetes," type 2 diabetes mellitus," "type II diabetes mellitus," "non-insulin-dependent diabetes," and "non-insulin-dependent diabetes mellitus (NIDDM)" are used interchangeably, and refer to a chronic diseases characterized by insulin resistance at the level of fat and muscle cells and resultant hyperglycemia.

The term "pathologic condition associated with type 2 diabetes" is used to refer to any condition that results, at least partially, from the long-term effects of type 2 diabetes. Such conditions include, without limitation, diabetic retinopathy, diabetic neuropathy, hypertension, atherosclerosis, diabetic ulcers, and in general damage caused to blood vessels, nerves and other internal structures by elevated blood sugar levels.

The term "obesity" is used to describe an excessive amount of body fat. Typically, a person is considered obese if he or she has a body mass index (BMI) of 30 kg/m$^2$ or greater.

The term "treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. Thus, in the case of obesity, the term "treatment" includes the treatment of obese subjects as well as preventative treatment of subjects a risk of developing obesity. Similarly, in the case of type 2 diabetes, "treatment" refers both to treating subjects diagnosed with type 2 diabetes and those at risk of developing type 2 diabetes.

The term "mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

B. Detailed Description

The present invention relates to new and improved methods for treating diabetes and/or its associated complications by modulating the activity of protein tyrosine phosphatase 1B ("PTP-1B"). The inventive compounds modulate the activity of PTP-1B by binding to a novel binding site (referred herein as "the PTP-1B exosite") that is distal to the active site of PTP-1B. Thus, in one aspect of the present invention, compounds are provided that bind to the exosite of PTP-1B. In another aspect of the present invention, methods are provided for using these compounds to modulate the activity of PTP-1B. In another aspect of the present invention, methods are provided of using an exosite inhibitor of PTP-1B to treat various disease conditions including diabetes, insulin resistance, and obesity.

The present invention also relates to methods for treating immune system disorders by modulating the activity of T-cell protein tyrosine phosphatase ("TC-PTP"). The inventive compounds modulate TC-PTP by binding to a novel binding site (referred herein as "the TC-PTP exosite") that is distal to the active site of TC-PTP. Thus, in one aspect of the present invention, compounds are provided that bind to the exosite of TC-PTP. In another aspect of the present invention, methods are provided for using these compounds to modulate the activity of TC-PTP. In another aspect of the present invention, methods are provided of using an exosite inhibitor of TC-PTP to treat various disease conditions including inflammation, immune system disorders, and hematopoietic disorders.

PTP-1B and TC-PTP are protein tyrosine phosphatases. Tyrosine phosphorylation is reversible and dynamic, and the equilibrium between phosphorylated and unphosphorylated protein is governed by the opposing activities of protein tyrosine kinases ("PTKs") that catalyze the addition of a phosphate group and protein tyrosine phosphatases ("PTPs") that catalyze the reverse activity or the removal of the added phosphate group.

The signature motif of a PTP is $(H/V)C(X)_5R(S/T)$ where X is any amino acid residue. See Zhang, *Current Opinions in Chemical Biology* 5: 416–423 (2001); and Zhang, *Annual Review of Pharmacology and Toxicology* 42: 209–234 (2002). The PTP signature motif is found in a critical loop (termed the PTP loop or P-loop) in the active site of the catalytic PTP domain and includes two (cysteine and arginine) of the three essential catalytic residues. The third catalytic residue is aspartic acid and is found in the WPD loop (also known as the flexible loop). In addition, all PTPs are characterized by their ability to hydrolyze p-nitrophenyl phosphate without the presence of a metal ion, sensitivity to vanadate, and insensitivity to okadaic acid.

The three-dimensional structures of the PTP domains are remarkably similar despite the variation in amino acid sequences and the differences in substrate specificity between the tyrosine-specific PTPs and the dual-specificity PTPs. The PTP domains, whose structures have been solved to date, are α/β domains that are composed of a highly twisted mixed β-sheet flanked by α-helices on both sides. Because of the similarity in the tertiary fold of PTP domains, the functional diversity of PTPs generally is a consequence of the presence of diverse noncatalytic regulatory and targeting domains that are found in the N and C termini of the PTP catalytic domain.

The active site of the PTP domain is located within a crevice on the molecular surface and is formed by several critical loops. Most of the 27 invariant residues in the sequences of the PTP domains are found on these loops. Invariant residues more distally located from the catalytic sites are buried and are believed to stabilize the protein domain's tertiary fold.

The mechanism for the hydrolysis reaction catalyzed by PTPs is believed to be follows. The phosphate group of pTyr is coordinated within the active site by main-chain amide groups and the Arg side chain of the PTP loop. The binding of pTyr to the active site induces a major conformational change of the WPD loop from the open form to the closed form that shifts as much as 8 Angstroms so that the aspartic acid within the WPD loop becomes properly positioned to act as a general acid in the hydrolysis reaction. The catalytic reaction begins with a nucleophilic attack by the cysteine (in the PTP loop) forming a cysteinyl-phosphate intermediate. Cleavage of the scissile phosphate-oxygen bond is facilitated by protonation of the phenolic oxygen by the aspartic acid in the WPD loop. The closed or the catalytically competent form (wherein the WPD loop occludes the active site) is believed to prevent non-specific phosphoryl transfer reactions to extraneous phosphoryl acceptors. In addition, the closed WPD loop is believed to play a role in activating a nucleophilic water molecule that ultimately hydrolyzes the cysteinyl-phosphate intermediate.

The discovery of the exosite in both PTP-1B and TC-PTP opens up an alternative route to modulating these important phosphatases. To date, all of the known drug programs targeting PTP-1B and TC-PTP have focused on identifying active site inhibitors. Although these programs generally have succeeded in identifying potent active site inhibitors against the target enzymes, achieving cell penetration (in view of the highly charged nature of most p-Tyr mimetics), selectivity and in vivo efficacy have been problematic. However, because the exosite is more hydrophobic in nature than the active site and generally is not conserved among phosphatases, cell penetration and selectivity can be attained much more readily. Moreover, because the exosite inhibitors do not have to compete with endogenous substrates, in vivo efficacy can be achieved with less potent compounds than the active site PTP inhibitors.

PTP-1B

PTP-1B has been shown to play a major role in modulating metabolism rates and insulin sensitivity. One of the most compelling studies implicating PTP-1B to diabetes and obesity is the knock-out study in mice. Elchebly et al., *Science* 283:1544–1548 (1999) and Klaman et al, *Mol. Cell. Biol.* 20: 5479–5489 (2000). Disruption of the mouse homolog of the gene encoding PTP-1B resulted in healthy mice. In the fasted state, no difference was detected between the PTP-1B deficient mice and the control mice in the concentrations of glucose or insulin. However, in the fed state, the PTP-1B deficient mice had slightly lower concentrations of glucose and approximately half the concentration of circulating insulin than those of the control mice. Moreover, when fed a high fat diet, the PTP-1B deficient mice were resistant to weight gain and remained insulin sensitive whereas the control mice gained weight rapidly and became insulin resistant. This and other subsequent studies have demonstrated PTP-1B as a validated target for the treatment of various metabolic disorders including diabetes and obesity.

Human PTP-1B is a 435 amino acid protein. The sequence comprises a short N-terminal sequence, a PTP domain and an ER anchor. Because the full-length protein is insoluble in bacteria, studies of PTP-1B typically have been on a 298 amino acid form or on a 321 amino acid form that was first isolated from human placenta. These truncated forms are fully functional in activity studies and is consistent with the crystallographic findings that only the first 298 residues are ordered.

TC-PTP

Human TC-PTP is a 415 amino acid protein that among other things is involved in hematopoiesis, and T- and B-cell activation. Two isoforms or splice variants of TC-PTP are expressed and differ only at their extreme C-termini. The splice variants appear to be a means for controlling the subcellular location of TC-PTP. The 48 kD variant contains a hydrophobic sequence of 34 residues as the C-terminus tail and is localized in the endoplasmic reticulum. Both residues 346–358 as well as the hydrophobic C-terminus tail are required to target this form of TC-PTP to the endoplasmic reticulum. In contrast, the 45 kD variant contains a hydrophilic sequence of 6 amino acids and is found primarily in the nucleus. Residues 350–358 and 377–381 are believed to form a bipartite nuclear localization signal.

FIG. 1 is a sequence alignment of human PTP-1B and TC-PTP. The sequences show a 68% identity between the first 298 residues of PTP-1B and the first 296 residues of TC-PTP. When referring to the TC-PTP sequence herein, following convention, it will be referred to using the PTP-1B based residue number system. For example, the catalytic cysteine in the active site of PTP-1B is Cys-215. The corresponding cysteine in TC-PTP is also referred to Cys-215 based on the sequence alignment with PTP-1B even though the active site cysteine is the $214^{th}$ amino acid if it were numbered consecutively.

The Exosite

In one aspect of the present invention, compounds are provided that bind to the exosite of PTP-1B. The exosite is an adaptive binding site on PTP-1B comprising at least one (more preferably at least two residues) selected from the group consisting of: Glu-186; Ser-187; Pro-188; Ala-189; Leu-192; Asn-193; Phe-196; Lys-197; Arg-199; Glu-200; Leu-272; Glu-276; Gly-277; Lys-279; Phe-280; Ile-281; and Met-282. In the presence of a suitable ligand, one or more of these residues form an adaptive binding site that is not normally present. For the purposes of illustration, the formation of this adaptive binding site that is referred herein as the exosite will be described with reference to the following compound

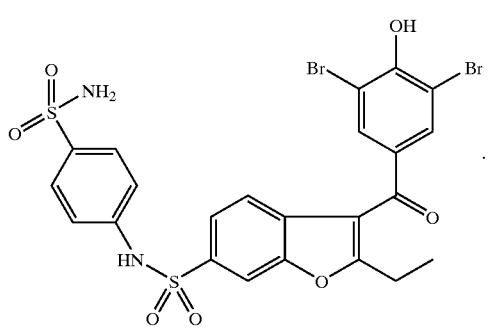

Figure 3:
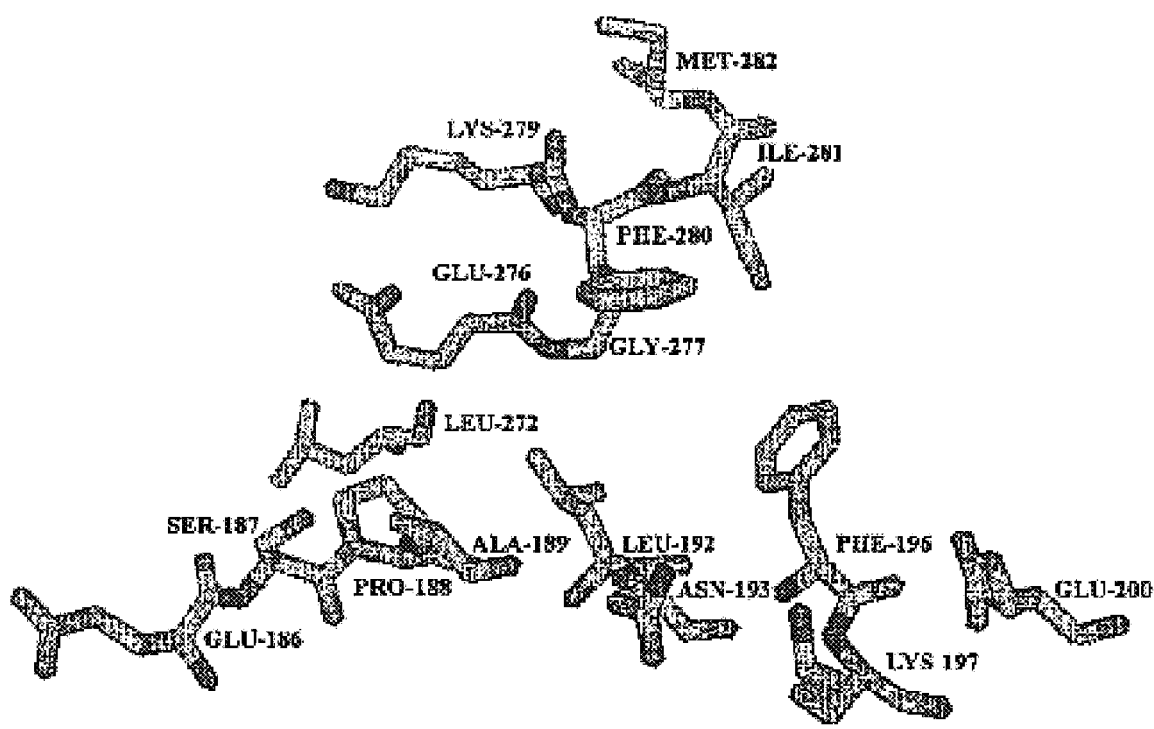
FIG. 3 shows the amino acids that comprise the exosite region of PTP-1B.

This compound binds to and inhibits PTP-1B with an IC$_{50}$ of about 30 μM. In the presence of compound 5 and as shown in FIG. 2, PTP-1B creates an exosite that is distal to the active site. The image in FIG. 2 is based upon the crystal complex of PTP-1B and compound 5. To highlight the presence of the crevice which forms the exosite binding site, the surface accessible surfaces are shown of residues Glu-186; Ser-187; Pro-188; Ala-189; Leu-192; Asn-193; Phe-196; Lys-197; Glu-200; Leu-272; Glu-276' Gly-277; Lys-279; Phe-280; Ile-281; and Met-282 (Arg-199 is not pictured in this view of the exosite). FIG. 3 is an illustration of the same region showing only the carbon and heteroatoms of residues Glu-186; Ser-187; Pro-188; Ala-189; Leu-192; Asn-193; Phe-196; Lys-197; Glu-200; Leu-272; Glu-276' Gly-277; Lys-279; Phe-280; Ile-281; and Met-282.

Figure 4:
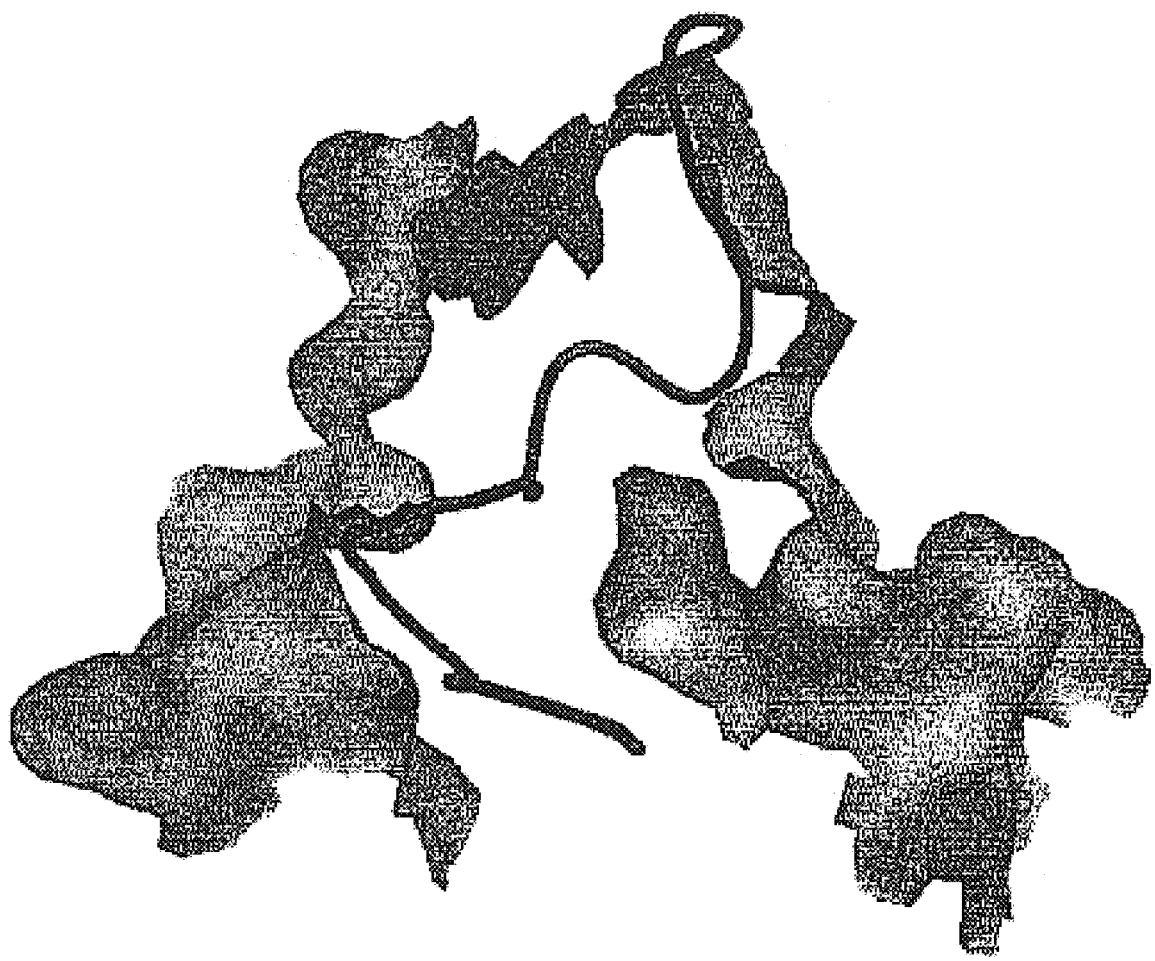
FIG. 4 is the same exosite region of PTP-1B as in FIG. 3 but in the absence of an exosite ligand. The accessible surface of the exosite-forming residues is shown. The structure that traverses and occludes the bulk of the exosite region is a helix formed by residues 283–298.

The exosite is referred to as an adaptive binding site because the presence of a suitable ligand induces major conformational rearrangement in the enzyme that creates the exosite binding site. In the absence of such a ligand, the presence of the exosite cannot be discerned or predicted given that these same residues do not form a contiguous surface accessible region. FIG. 4 is a crystal structure of residues 1–298 of PTP-1B in the absence of an exosite ligand. As it can be seen, the majority of the exosite region is no longer surface accessible as it is occluded by the presence of a helix formed by residues 283–298.

Figure 5:
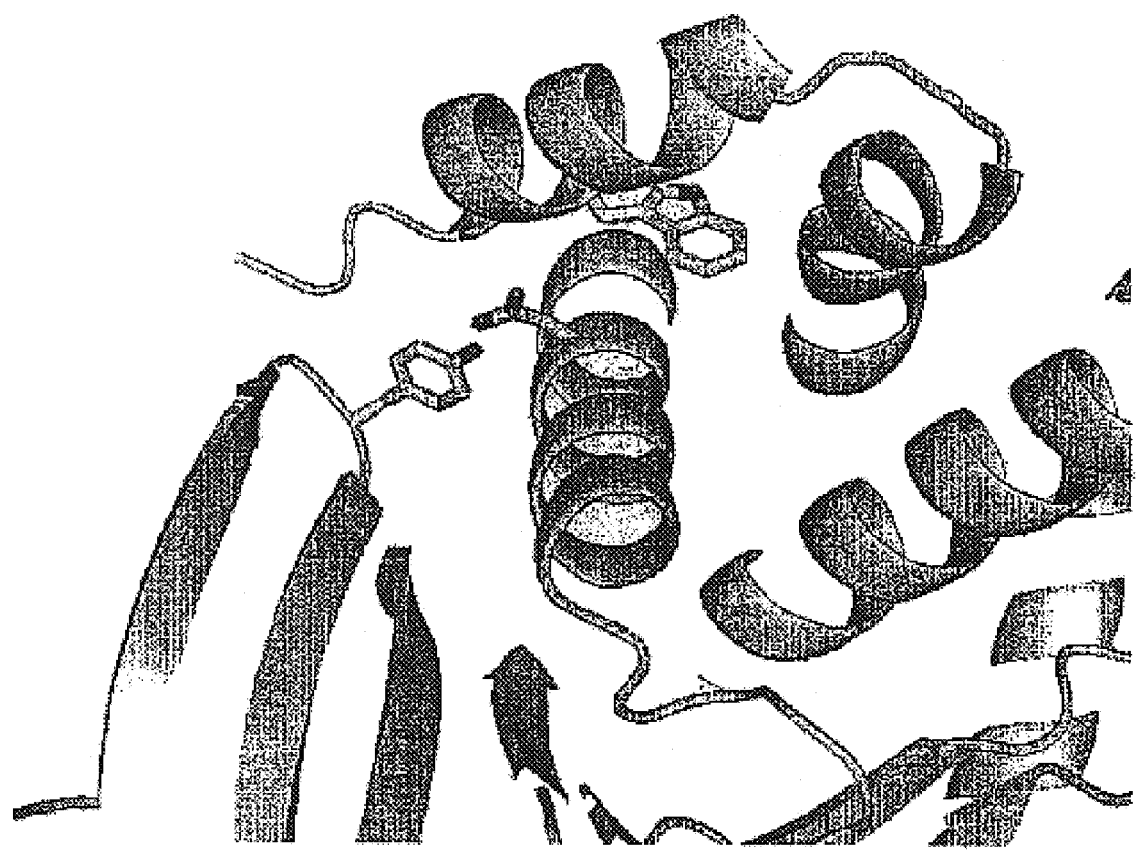
FIG. 5 is a ribbon diagram of PTP-1B in the absence of an exosite ligand where Tyr-152, Asn-193, and Trp-291 are highlighted.

The large conformational change that occurs in the presence of an exosite ligand is mediated by the interactions of at least three residues: Tyr-152, Asn-193, and Trp-291 and is believed to be part of a regulatory mechanism for PTP-1B. FIG. 5 illustrates a few of the key interactions of these residues in the absence of an exosite ligand. The N$_{δ2}$ of Asn-193 makes a hydrogen bond with the Oη of Tyr-152 and the helix formed by residues 283–298 is maintained in position at least in part from the non-bonded interactions of the indole ring of Trp-291 with the phenyl rings of Phe-280 and Phe-196 (not pictured). A fourth residue, Lys-197 (not pictured), is also believed to participate in maintaining the hydrogen bond interaction between the N$_{δ2}$ of Asn-193 and Oη of Tyr-152.

Figure 6:
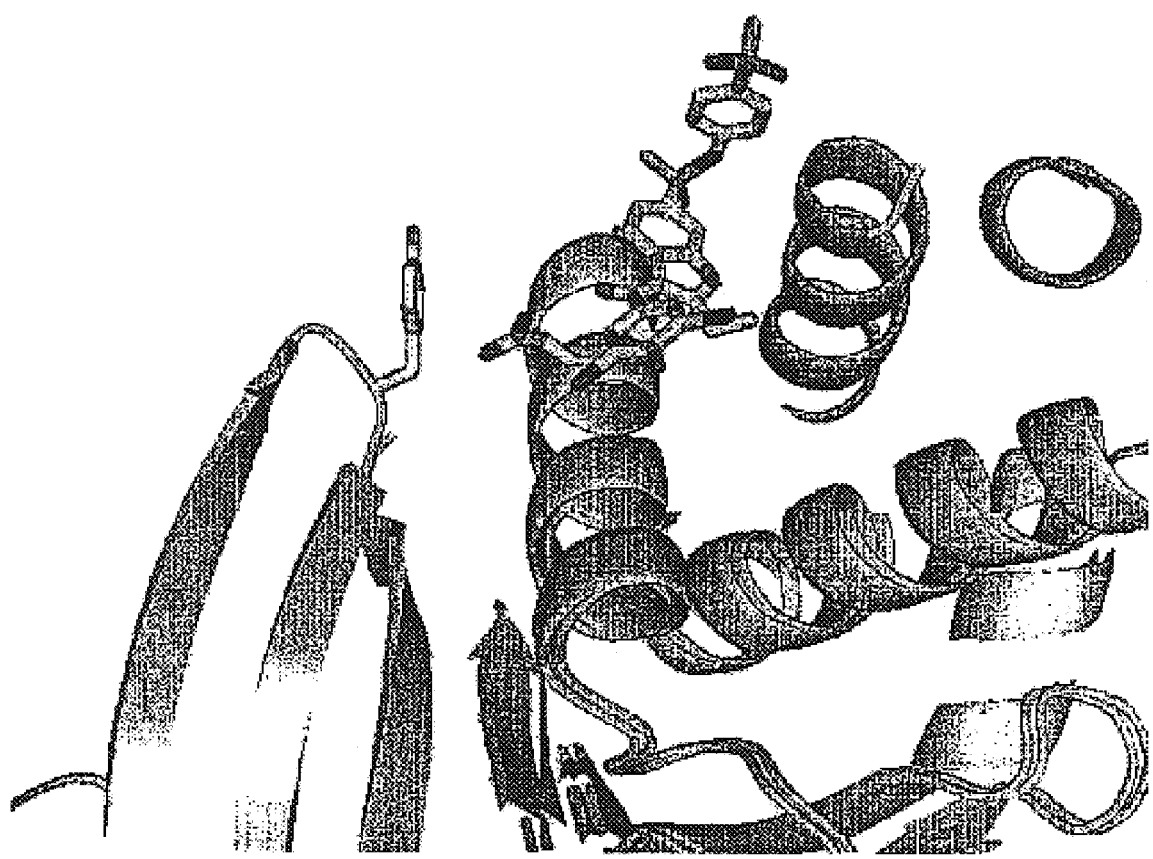
FIG. 6 is a ribbon diagram of PTP1B in the presence of exosite ligand 5 where Tyr-152, Asn-193, and Tryp-291 are highlighted.

In contrast, FIG. 6 illustrates the situation in the presence of exosite ligand 5. As it can be seen, the benzofuran moiety of compound 5 displaces the indole ring of Trp-291 causing the helix formed by residues 283–298 to become displaced and/or disordered. The carbonyl oxygen of compound 5 makes a hydrogen bond with N$_{δ2}$ of Asn-193 so that the N$_{δ2}$ of Asn-193 is no longer available for hydrogen bonding to Oη of Tyr-152. The disruption of the hydrogen bond between Asn-193 and Tyr-152 in part mediates a conformation change in the phenolic ring of Tyr-152. The rotation of the phenolic ring of Tyr-152 propagates a conformational change in the active site of PTP-1B that functionally inactivates the enzyme.

The importance of the three key residues, particularly the interaction between Asn-193 and Tyr-152, is supported by the ability (or lack thereof) of compound 5 to bind to the exosite of and inhibit other phosphatases. In TC-PTP, many of the exosite-forming residues of PTP-1B are conserved including Asn-193, Lys-197 and Tyr-152. Not surprising, compound 5 also inhibits TC-PTP, although with a slightly lower potency than that observed for PTP-1B (IC$_{50}$ of about 130 μM). In contrast, compound 5 does not inhibit tyrosine phosphatase leukocyte common antigen related protein ("LAR") where the exosite-forming residues of PTP-1B generally are not conserved including Asn-193, Lys-197, and Tyr-152. A sequence alignment of PTP-1B and LAR is shown in FIG. 7.

Exosite Inhibitors and Methods of Identifying the Same

In one aspect of the present invention, compounds are provided that interact with at least one residue (preferably at least two residues and more preferably at least three residues) selected from the group consisting of: Glu-186; Ser-187; Pro-188; Ala-189; Leu-192; Asn-193; Phe-196; Lys-197; Arg-199; Glu-200; Leu-272; Glu-276; Gly-277; Lys-279; Phe-280; Ile-281; and Met-282 of PTP-1B (collectively referred to as "PTP-1B exosite-forming residues"). The resulting exosite ligand-PTP-1B complex is considered another aspect of the present invention. In one embodiment embodiment, compounds are provided that interact with at least one residue (preferably at least two residues and more preferably at least three residues) selected from the group consisting of Asn-193, Phe-196, Lys-197, Arg-199; Glu-276, and Phe-280 of PTP-1B. In another embodiment, the interaction between the compound and the PTP-1B exosite-forming residues comprises an interaction between the compound and Asn-193 and Phe-196. In yet another embodiment, the interaction between the compound and the PTP-1B exosite forming residues comprises an interaction between the compound and Asn-193 and Phe-280.

In another aspect of the present invention, compounds are provided that interact with at least one residue (preferably at least two residues and more preferably at least three residues) selected from the group consisting of: Glu-186; Ser-187; Pro-188; Ala-189; Leu-192; Asn-193; Phe-196; Lys-197; Arg-199; Glu-200; Met-272; Glu-276; Gly-277; Lys-279; Cys-280; Ile-281; and Lys-282 of TC-PTP (collectively TC-PTP exosite-forming residues). The resulting exosite ligand-TC-PTP complex is considered another aspect of the present invention. In one embodiment, compounds are provided that interact with at least one residue (preferably at least two residues and more preferably at least three residues) selected from the group consisting of Asn-193; Phe-196; Lys-197; Arg-199; Glu-276; and Cys-280 of TC-PTP. In another embodiment, the interaction between the compound and the TC-PTP exosite-forming residues comprises an interaction between the compound and Asn-193 and Phe-196. In yet another embodiment, the interaction between the compound and the TC-PTP exosite-forming residues comprises an interaction between the compound and Asn-193 and Cys-280.

A compound is said to interact with an exosite-forming residue (whether PTP-1B or TC-PTP) if the compound forms a hydrogen bond, a salt bridge, or a van der Waals contact with an exosite-forming residue. A compound is considered to form a hydroxyl-hydroxyl or hydroxyl-carbonyl hydrogen bond if the distance between the donor and acceptor atom is between about 2.5 Angstroms and about 3.0 Angstroms. A compound is considered to form an amide-carbonyl, amide-hydroxyl, or amide-imidazole hydrogen bond if the distance between the donor and acceptor atom is about 2.7 Angstroms and 3.3 Angstroms. A compound is considered to form a amide-sulfur hydrogen bond if the distance between the donor and acceptor atom is between about 3.3 Angstroms and 3.9 Angstroms.

A compound is considered to form a salt bridge with an exosite-forming residue if the distance between an amino (ionized) group and a carboxylic acid (ionized) group is about 2.5 Angstroms to about 4.0 Angstroms.

A compound is considered to make a van der Waals contact if the distance between a carbon or a heteroatom in the compound and a carbon or a heteroatom in an exosite-forming residue is between about 2.0 Angstroms to about 5.0 Angstroms (preferably between about 2.5 Angstroms to about 4.0 Angstroms, and more preferably between about 2.5 and about 3.5 Angstroms).

In another embodiment, the compound (whether it is an exosite ligand of PTP-1B or TC-PTP) is an "isolated" compound. As used herein, the term "isolated" means purified (at least 80% pure, preferably at least 90% pure, more preferably at least 95% pure, and most preferably at least 99% pure as measured by weight). The term "isolated" with respect to naturally occurring compounds such as polypeptides includes any state that is not naturally occurring. Examples of a state that is not naturally occurring with respect to a polypeptide are purified or recombinant forms of that polypeptide. In another embodiment, the compound is not a polypeptide. In yet another embodiment, the compound does not include an amino acid residue.

In another aspect of the present invention, methods are provided for identifying compounds that bind to the exosite of PTP-1B and inhibit the activity of PTP-1B. In one embodiment, the method comprise:

a) contacting a test compound with PTP-1B;

b) contacting the test compound with an exosite mutant of PTP-1B; and c) comparing the activity of PTP-1B in the presence of the test compound with the activity of the exosite mutant of PTP-1B in the presence of the test compound.

PTP-1B for the purposes of these methods is wild-type PTP-1B or any functional truncated form thereof (e.g., a form that is capable of dephosphorylating a phosphotyrosine and includes all of the native exosite-forming residues). In one embodiment, the PTP-1B is human PTP-1B. In another embodiment, the PTP-1B comprises SEQ ID. NO. 1.

An exosite mutant of PTP-1B is a PTP-1B wherein at least one of the PTP-1B exosite-forming residues has been modified to a different amino acid such that the resulting PTP-1B is no longer capable of being inhibited through the exosite site or displays a diminished capacity (less than about 75% inhibition compared to SEQ ID NO. 1 for a known exosite inhibitor such as compound 5; preferably less than about 50%, more preferably less than about 25%) of being inhibited through the exosite. Exosite mutants of PTP-1B comprise another aspect of the present invention.

In one embodiment, the exosite mutant of PTP-1B is PTP-1B wherein Asn-193 has been mutated to another amino acid. In another embodiment, the exosite mutant of PTP-1B is PTP-1B wherein Asn-193 has been mutated to alanine. In another embodiment, the exosite mutant of PTP-1B is PTP-1B wherein Lys-197 has been mutated to another amino acid. In another embodiment, the exosite mutant of PTP-1B is PTP-1B wherein Lys-197 has been mutated to cysteine. In another embodiment, the exosite mutant of PTP-1B is PTP-1B wherein Asn-193 and Phe-196 have been mutated. In another embodiment, the exosite mutant of PTP-1B is PTP-1B wherein Asn-193 has been mutated to alanine and Lys-197 has been mutated to cysteine. In another embodiment, the exosite mutant of PTP-1B is PTP-1B wherein Asn-193 has been mutated to alanine and Phe-196 has been mutated to arginine. In another embodiment, the exosite mutant of PTP-1B is PTP-1B wherein Asn-193, Phe-196, and Phe-280 have been mutated. In another embodiment, the exosite mutant of PTP-1B is PTP-1B wherein Asn-193 is mutated to alanine, Phe-196 has been mutated to arginine and Phe-280 has been mutated to cysteine.

Test compounds that inhibit PTP-1B but not an exosite mutant of PTP-1B are potential exosite inhibitors. Compounds that inhibit PTP-1B in a non-competitive manner with active site ligands and that inhibit PTP-1B in a competitive manner with known exosite ligands such as compound 5 are PTP-1B exosite inhibitors.

In another aspect of the present invention, methods are provided for finding compounds that bind to the exosite of TC-PTP and inhibit the activity of TC-PTP. In one embodiment, the method comprise:

a) contacting a test compound with TC-PTP;

b) contacting the test compound with an exosite mutant of TC-PTP; and c) comparing the activity of TC-PTP in the presence of the test compound with the activity of the exosite mutant of TC-PTP in the presence of the test compound.

TC-PTP for the purposes of these methods is wild-type TC-PTP or any functional truncated form thereof (e.g., a form that is capable of dephosphorylating a phosphotyrosine and includes all of the native exosite-forming residues). In one embodiment, the TC-PTP is human TC-PTP. In another embodiment, the TC-PTP comprises SEQ ID. NO. 2.

An exosite mutant of TC-PTP is a TC-PTP wherein at least one of the TC-PTP exosite-forming residues has been modified to a different amino acid such that the resulting TC-PTP is no longer capable of being inhibited through the exosite site or displays a diminished capacity (less than about 75% inhibition compared to SEQ ID NO. 2 for a known exosite inhibitor such as compound 5; preferably less than about 50%; and more preferably less than about 25%) of being inhibited through the exosite. Exosite mutants of TC-PTP comprise another aspect of the present invention.

In one embodiment, the exosite mutant of TC-PTP is TC-PTP wherein Asn-193 has been mutated to another amino acid. In another embodiment, the exosite mutant of TC-PTP is TC-PTP wherein Asn-193 has been mutated to alanine. In another embodiment, the exosite mutant of TC-PTP is TC-PTP wherein Lys-197 has been mutated to another amino acid. In another embodiment, the exosite mutant of TC-PTP is TC-PTP wherein Lys-197 has been mutated to a cysteine. In another embodiment, the exosite mutant of TC-PTP is TC-PTP wherein Asn-193 and Phe-196 have been mutated. In one embodiment, the exosite mutant of TC-PTP is TC-PTP wherein Asn-193 has been mutated to alanine and Phe-196 has been mutated to arginine. In another embodiment, the exosite mutant of TC-PTP is TC-PTP wherein Asn-193 and Lys-197 have been mutated. In another embodiment, the exosite mutant of TC-PTP is TC-PTP wherein Asn-193 has been mutated to alanine and Lys-197 has been mutated to cysteine.

Test compounds that inhibit TC-PTP but not mutant TC-PTP are potential TC-PTP exosite inhibitors. Compounds that inhibit TC-PTP in a non-competitive manner with active site ligands and that inhibit TC-PTP in a competitive manner with exosite ligands are TC-PTP exosite inhibitors.

Compounds of the Present Invention

In another aspect of the present invention, compounds are provided having the structure

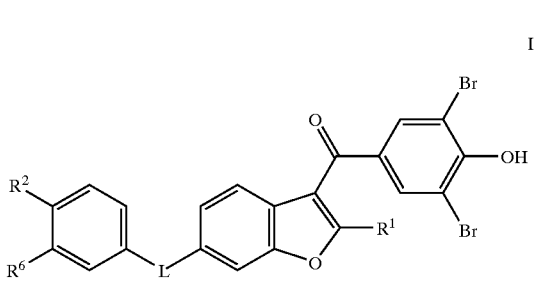

wherein:
R[1] is hydrogen, methyl, ethyl, or propyl;
R[2] is hydrogen, —S(O$_2$)R[3], —NHC(=O)R[3], —NHC(=O)CH$_2$(C=O)OR[3], —S(O$_2$)NR[4]R[5], or —NR[4]S(O$_2$)R[3] where R[3] is $C_1$–$C_5$ alkyl, R[4] is hydrogen, $C_1$–$C_5$ alkyl, unsubstituted cyclic moiety, or substituted cyclic moiety, and R[5] is either hydrogen or R[5] and R[4] together form an unsubstituted cyclic moiety or a substituted cyclic moiety;
R[6] is hydrogen or alternatively when R[2] is —NR[4]S(O$_2$)NR[3], then R[6] and R[4] together form an unsubstituted cyclic moiety or substituted cyclic moiety; and,
L is —NHS(O$_2$)— or —S(O$_2$)NR[7]CH$_2$— where R[7] is hydrogen or $C_1$–$C_5$ alkyl.

In one embodiment, the compounds are of structure I wherein the one or more substituents on the substituted cyclo group are each independently selected from the group consisting of: $C_1$–$C_5$ alkyl, phenyl, benzyl, F, Cl, I, Br, —OH; —NO$_2$; —CN; —CF$_3$; —CH$_2$CF$_3$; —CH$_2$Cl; —CH$_2$OH; —CH$_2$CH$_2$OH; —CH$_2$NH$_2$; —CH$_2$SO$_2$CH$_3$; —OR[8]; —C(O)R[8]; —COOR[8]; —C(O)NR[8]R[9]; —OC(O)R[8]; —OCOOR[8]; —OC(O)NR[8]R[9]; —NR[8]R[9]; —S(O)$_2$R[8]; and —NR[8]C(O)R[9] where R[8] and R[9] are each independently hydrogen, $C_1$–$C_5$ alkyl, phenyl or benzyl.

In another embodiment, the compounds are of structure I wherein R[1] is ethyl.

In another embodiment, the compounds are of structure I wherein R[2] and R[6] are both hydrogen.

In another embodiment, the compounds are of structure I wherein R[2] is —S(O$_2$)NHR[5] where R[5] is an unsubstituted cyclic moiety or substituted cyclic moiety, and R[6] is hydrogen. In another embodiment the cyclic moiety is morpholine or piperidine. In another embodiment, the cyclic moiety is an aryl group. In another embodiment, the cyclic moiety is phenyl. In another embodiment, the cyclic moiety is a 5-membered heteroaryl. In another embodiment, the cyclic moiety is an imidazole, oxazole, or thiazole. In another embodiment, the cyclic moiety is a 6-membered heteroaryl. In another embodiment, the cyclic moiety is pyridine, pyrimidine, or pyrazine.

In another embodiment, the compounds are of structure I wherein R[2] is —S(O$_2$)R[3] where R[3] is methyl, ethyl, or propyl, and R[6] is hydrogen.

In another embodiment, the compounds are of structure I wherein R[2] is —NHC(=O)R[3] where R[3] is methyl, ethyl, or propyl, and R[6] is hydrogen.

In another embodiment, the compounds are of structure I wherein R[2] is —NHC(=O)CH$_2$(C=O)OR[3] where R[3] is methyl, ethyl, or propyl, and R[6] is hydrogen.

In another embodiment, the compounds are of structure I wherein R[2] is —NR[4]S(O$_2$)R[3] wherein R[3] is methyl and R[4] and R[6] together form an unsubstituted heterocyclo or a substituted heterocyclo. In another embodiment R[4] and R[6] together form an unsubstituted pyrrolidine or a substituted pyrrolidine.

In another embodiment, the compounds are of structure I wherein L is —NHS(O$_2$)—.

In another embodiment, the compounds are of structure I wherein L is —S(O$_2$)NR[7]CH$_2$— and R[7] is methyl.

In another embodiment, the compounds are of structure I wherein L is —S(O$_2$)NR[7]CH$_2$— and R[7] is ethyl.

In another embodiment, the compounds are of structure I wherein L is —S(O$_2$)NR[7]CH$_2$— and R[7] is propyl.

In another aspect of the present invention, compounds are provided having the following structure:

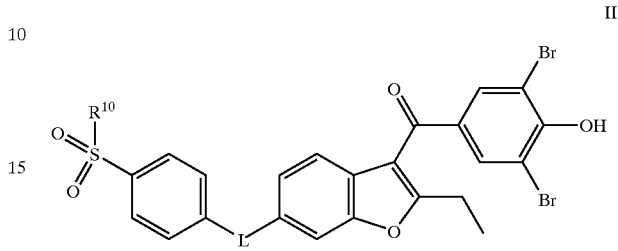

wherein:
R[10] is $C_1$–$C_5$ alkyl or NHR[11] where R[11] is hydrogen, $C_1$–$C_{10}$ alkyl or aryl; and,
L is —NHS(O$_2$)— or —S(O$_2$)NH(CH$_2$)$_3$CH$_2$—.

In one embodiment, the compounds are of structure II and R[10] is methyl, ethyl or propyl.

In another embodiment, the compounds are of structure II and R[10] is NHR[11]. In another embodiment, R[11] is hydrogen. In another embodiment R[11] is aryl. In another embodiment, R[11] is a heteroaryl. In another embodiment, R[11] is phenyl. In another embodiment, R[11] is thiazole. In another embodiment, R[11] is pyrimidine.

It will be appreciated by one of ordinary skill in the art that compounds of the present invention include one or more asymmetric centers. The inventive compounds may be in the form of an individual enantiomer, diasteromer or geometric isomer, or may be in the form of a mixture of stereoisomers unless otherwise indicated. In the case of compounds containing double bonds, these double bonds can be either Z or E or a mixture thereof, unless otherwise indicated.

As used herein "aliphatic" or "unsubstituted aliphatic" refers to a straight, branched, cyclic, or polycyclic hydrocarbon and includes alkyl, alkenyl, alkynyl, cycloalkyl, cycloalkenyl, and cycloalkynyl moieties.

The term "alkyl" or "unsubstituted alkyl" refers to a saturated hydrocarbon.

The term "alkenyl" or "unsubstituted alkenyl" refers to a hydrocarbon with at least one carbon—carbon double bond.

The term "alkynyl" or "unsubstituted alkynl" refers to a hydrocarbon with at least one carbon—carbon triple bond.

The term "aryl" or "unsubstituted aryl" refers to a mono or polycyclic unsaturated moieties having at least one aromatic ring. The term includes heteroaryls that include one or more heteroatoms within the at least one aromatic ring. Illustrative examples of aryl include: phenyl, naphthyl, tetrahydronaphthyl, indanyl, indenyl, pyridyl, pyrazinyl, pyrimidinyl, pyrrolyl, pyrazolyl, imidazolyl, thiazolyl, oxazolyl, isooxazoly, thiadiazolyl, oxadiazolyl, thiophenyl, furanyl, quinolinyl, isoquinolinyl, and the like.

The term "alkylaryl" or "unsubstituted alkylaryl" refers to an aryl moiety that is substituted with at least one aliphatic group.

The term "cyclo" or "cyclic moiety" refers to a mono or polycyclic aliphatic or aromatic groups. The cyclic aliphatic groups include partially unsaturated cyclic moieties (having one or more double or triple bonds). The term includes heterocyclic and heteroaryl groups.

The term "substituted moiety" refers to a substituted version of the moiety where at least one hydrogen atom is substituted with another group including but not limited to:

aliphatic; aryl, alkylaryl, F, Cl, I, Br, —OH; —NO$_2$; —CN; —CF$_3$; —CH$_2$CF$_3$; —CH$_2$Cl; —CH$_2$OH; —CH$_2$CH$_2$OH; —CH$_2$NH$_2$; —CH$_2$SO$_2$CH$_3$; —OR$^x$; —C(O)R$^x$; —COOR$^x$; —C(O)NR$^x$R$^y$; —OC(O)R$^x$; —OCOOR$^x$; —OC(O)NR$^x$R$^y$; —NR$^x$R$^y$; —S(O)$_2$R$^x$; and —NR$^x$C(O)R$^y$ where R$^x$ and R$^y$ are each independently hydrogen, substituted aliphatic, unsubstituted aliphatic, substituted aryl, or unsubstituted aryl. Additionally, substitutions at adjacent groups on a moiety can together form a cyclic group.

Pharmaceutical Compositions

The present invention provides compounds useful among other things for treating obesity, diabetes and pathological conditions associated with type 2 diabetes, such as insulin resistance, in the case of PTP-1B inhibitors, and for treating inflammation, and hematopoietic and immunological disorders in the case of TC-PTP. Hematopietic disorders include, without limitation, disorders associated with impaired B cell lymphopoiesis and/or erythropoiesis.

In one aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. These therapeutic agents can include other anti-diabetes drugs in the case of PTP-1B inhibitors and can include other agents that modulate the immune response in the case of TC-PTP. Alternatively, the additional therapeutic agents can be those that alleviate or mitigate any side effect of the compounds of the present invention.

The term "pharmaceutically acceptable derivative" is any pharmaceutically acceptable salt, ester, or salt of such ester, of a compound (or any other adduct or derivative) that, upon administration to a patient, is capable of providing (directly or indirectly) the desired compound. Pharmaceutically acceptable derivatives includes among other things, prodrugs—a derivative of a compound that typically contains an additional moiety that is removed in vivo yielding the parent molecule as the pharmacologically active species.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66: 1–19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A discussion is provided in T. Higuchi and V. Stella, Pro-drugs as Novel Delivery Systems, Vol. 14 of the A. C. S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally can comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Methods of Use and Dosage Forms

In another aspect of the present invention, a method for treating diabetes is provided comprising administering to a subject in need thereof a therapeutically effective amount of a PTP-1B exosite inhibitor.

In another aspect of the present invention, a method for treating insulin resistance is provided comprising administering to a subject in need thereof a therapeutically effective amount of a PTP-1B exosite inhibitor.

In another aspect of the present invention, a method for treating diabetes is provided comprising administering to a subject in need thereof a therapeutically effective amount of a PTP-1B exosite inhibitor.

In another aspect of the present invention, a method for treating inflammation is provided comprising administering to a subject in need thereof a therapeutically effective amount of a TC-PTP exosite inhibitor.

In another aspect of the present invention, a method for treating immune system disorders is provided comprising administering to a subject in need thereof a therapeutically effective amount of a TC-PTP exosite inhibitor.

In yet another aspect of the present invention, a method for treating a hematopoiesis disorder is provided comprising administering to a subject in need thereof a therapeutically effective amount of a TC-PTP exosite inhibitor.

The term subject refers to a mammal, more preferably a human.

The term "effective amount" refers to an amount of a compound that will elicit the biological or medical response of subject that is being sought by a researcher or clinician. The term "therapeutically effective amount" means any amount which, as compared to a corresponding subject who has not received such amount, results in improved treatment, healing, prevention, or amelioration of a disease or disorder, or a decrease in the rate of advancement of a disease or disorder, and also includes amounts effective to enhance normal physiological function. The exact amount required will vary from subject to subject, depending on the species, age, and general condition of the subject, the severity of the infection, the particular therapeutic agent, its mode of administration, and the like.

The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50–100 mg/kg) can be administered to a subject. In certain embodiments, compounds are administered orally or parenterally.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides).

Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent for example), or they may achieve different effects (e.g., control of any adverse effects).

EXAMPLE 1

Cloning of PTP-1B

Truncated versions of wildtype human PTP-1B were made as follows. A cDNA encoding the first 321 amino acids of human PTP-1B (SEQ ID NO: 4) was isolated from human fetal heart total RNA (Clontech).

```
                                                 SEQ ID NO. 4:
MEMEKEFEQIDKSGSWAAIYQDIRHEASDFPCRVAKLPKNKNRNRYRDVS

PFDHSRIKLHQEDNDYINASLIKMEEAQRSYILTQGPLPNTCGHFWEMVW

EQKSRGVVMLNRVMEKGSLKCAQYWPQKEEKEMIFEDTNLKLTLISEDIK

SYYTVRQLELENLTTQETREILHFHYTTWPDFGVPESPASFLNFLFKVRE

SGSLSPEHGPVVVHCSAGIGRSGTFCLADTCLLLMDKRKDPSSVDIKKVL

LEMRKFRMGLIQTADQLRFSYLAVIEGAKFIMGDSSVQDQWKELSHEDLE

PPPEHIPPPPRPPKRILEPH
```

Oligonucleotide primers corresponding to nucleotides 91 to 114 (For) and complementary to nucleotides 1030 to 1053 (Rev) of the PTP-1B cDNA (Genbank M31724.1; Chernoff, J. et. al., *Proc. Natl. Acad. Sci. U.S.A.* 87: 2735–2739 (1990)) were synthesized and used to generate a DNA using the polymerase chain reaction.

```
                                              (SEQ ID NO: 5)
Forward:   GCCATATGGAGATGGAAAAGGAGTTC GAG (SEQ ID NO: 6)
Reverse:   GCGACGCGAATTCTTAATTGTGTGGCTCCAGGATTCGTTT
```

The primer Forward incorporates an NdeI restriction site at the first ATG codon and the primer Rev inserts a UAA stop codon followed by an EcoRI restriction site after nucleotide 1053. cDNAs were digested with restriction nucleases NdeI and EcoRI and cloned into pRSETc (Invitrogen) using standard molecular biology techniques. The identity of the isolated cDNA was verified by DNA sequence analysis.

A shorter cDNA, PTP-1B 298, encoding amino acid residues 1–298 was generated using oligonuclotide primers Forward and Rev2 and the clone described above as a template in a polymerase chain reaction.

```
                                              (SEQ ID NO:7)
Reverse 2:  TGCCGGAATTCCTTAGTCCTCGTGGGAAAGCTCC
```

EXAMPLE 2
PTP-1B Mutants

The following mutants were made as follows. The 321 amino acid form of PTP-1B (SEQ ID NO: 3) in pRSETc (Invitrogen) was used as a template and T7 and RSETrev primers were used as "outside" primers.

```
PTP-1B[321; N193A; F196R]:
                                               SEQ ID. NO: 8
Fwd primer: TTCTTGGCGTTTCTTCGCAAAGTCCGA
                                               SEQ ID. NO: 9
Rev primer: GACTTTGCGAAGAAACGCCAAGAATGA PTP-1B[321; F280C]
                                              SEQ ID. NO: 10
Fwd primer: GGTGCCAAATGCATCATGGGG
                                              SEQ ID. NO: 11
Rev primer: CCCCATGATGCATTTGGCACC
```

PTP-1B[321; N193A; F196R; F280C] was generated by joining an NdeI-PstI fragment from PTP-1B[321; N193A; F196R], corresponding to residues 1–215, with a PstI-EcoRI fragment from PTP-1B[321; F280C], corresponding to residues 216–321.

PTP-1B[298; N193A; F196R; F280C] was generated by PCR using PTP-1B[321; N193A; F196R; F280C] as a template. T7 vector primer was used as forward primer and truncation at residue 298 was generated using the primer:

```
TGCCGGAATTCCTTAGTCCTCGTGCGAAAGCTCC    (SEQ ID NO:12)
```

The following mutants were made using Kunkel mutagenesis and PTP-1B[298] as a template.

```
E186C  GAATGAGGCTGGTGAGCAAGGGACTCCAAAG   SEQ ID NO: 13
S187C  GAATGAGGCTGGGCATTCAGGGACTCC       SEQ ID NO: 14
A189C  GTTCAAGAATGAGCATGGTGATTCAGG       SEQ ID NO: 15
K197C  CTGACTCTCGGACGCAGAAAAGAAAGTTC     SEQ ID NO: 16
E200C  GAGTGACCCTGAGCATCGGACTTTGAAAAG    SEQ ID NO: 17
C215S  GATGCCTGCACTGGAGTGCACCACAAC       SEQ ID NO: 18
M258C  CTGGATCAGCCCACACCGAAACTTCCT       SEQ ID NO: 19
Q262C  CTGGTCGGCTGTACAGATCAGCCCCAT       SEQ ID NO: 20
L272C  CTTCGATCACAGCGCAGTAGGAGAAGCG      SEQ ID NO: 21
E276C  GAATTTGGCACCGCAGATCACAGCCAG       SEQ ID NO: 22
I281C  AGAGTCCCCCATGCAGAATTTGGCACC       SEQ ID NO: 23
V287C  CCACTGATCCTGGCAGGAAGAGTCCCC       SEQ ID NO: 24
```

Besides mutations to cysteines, mutations removing naturally occurring cysteines (referred to as "scrubs") can also be made. For example, naturally occurring cysteines at positions 92 and 121 can be mutated to other residues such as alanine or serine. Illustrative examples of oligos for this purpose include:

```
C92A   CCAAAAGTGACCGGCTGTGTTAGGCAA       SEQ ID NO: 25
C121A  CCAGTATTGTGCGGCTTTTAACGAACC       SEQ ID NO: 26
C121S  CCAGTATTGTGCGCTTTTTAACGAACC       SEQ ID NO: 27
```

Sequencing of PTP-1B clones was accomplished as follows. The concentration of plasmid DNA was quantitated by absorbance at 280 nm. 1000 ng of plasmid was mixed with sequencing reagents (1 μg DNA, 6 μl water, 1 μl sequencing primer at 3.2 pm/μl, 8 μl sequencing mixture with Big Dye [Applied Biosystems]). The sequencing primers are SEQ ID NO: 28 and SEQ ID NO: 29.

```
Forward primer, "T7"
AATACGACTCACTATAG                     SEQ ID NO: 28

Reverse primer, "RSET REV"
TAGTTATTGCTCAGCGGTGG                  SEQ ID NO: 29
```

The mixture was then run through a PCR cycle (96° C., 10 s; 50° C., 5 s; 60° C., 4 minutes; 25 cycles) and the DNA reaction products were precipitated (20 μl mixture, 80 μl 75% isopropanol; incubated 20 minutes at room temperature then pelleted at 14 K rpm for 20 minutes; wash with 250 μl 75% isopropanol; heat 1 minute at 94° C.). The precipitated products were then resuspended in 20 μl TSB (Applied Biosystems) and the sequence read and analyzed by an Applied Biosystems 310 capillary gel sequencer. In general, ¼ of the plasmids contained the desired mutation.

Expression of Cysteine Mutants of PTP1

Mutant proteins were expressed as follows. PTP-1B clones were transformed into BL21 codon plus cells (Stratagene) (1 μl double-stranded DNA, 2 μl 5×KCM, 7 μl water, 10 μl DMSO competent cells; incubate 20 minutes at 4° C., 10 minutes at room temperature), plated onto LB/agar containing 100 μg/ml ampicillin, and incubated at 37° C. overnight. 2 single colonies were picked off the plates or from frozen glycerol stocks of these mutants and inoculated in 100 ml 2YT with 50 μg/ml carbenicillin and grown overnight at 37° C. 50 ml from the overnight cultures were added to 1.5 L of 2YT/carbenicillin (50 μg/ml) and incubated at 37° C. for 3–4 hours until late-log phase (absorbance at 600 nm~0.8–0.9). At this point, protein expression was induced with the addition of IPTG to a final concentration of 1 mM. Cultures were incubated at 37° C. for another 4 hours and then cells were harvested by centrifugation (7K rpm, 7 minutes) and frozen at −20° C.

PTP-1B proteins were purified from the frozen cell pellets as described in the following. First, cells were lysed in a microfluidizer in 100 ml of buffer containing 20 mM MES pH 6.5, 1 mM EDTA, 1 mM DTT, and 10% glycerol buffer (with 3 passes through a Microfluidizer [Microfluidics 110S]) and inclusion bodies were removed by centrifugation (10K rpm, 10 minutes). Purification of all PTP-1B mutants was performed at 4° C. The supernatants from the centrifugation were filtered through 0.45 μm cellulose acetate (5 μl of this material was analyzed by SDS-PAGE) and loaded onto an SP Sepharose fast flow column (2.5 cm diameter×14 cm long) equilibrated in Buffer A (20 mM MES pH 6.5, 1 mM EDTA, 1 mM DTT, 1% glycerol) at 4 ml/min.

The protein was then eluted using a gradient of 0–50% Buffer B over 60 minutes (Buffer B: 20 mM MES pH 6.5, 1 mM EDTA, 1 mM DTT, 1% glycerol, 1 M NaCl). Yield and purity was examined by SDS-PAGE and, if necessary, PTP-1B was further purified by hydrophobic interaction chromatography (HIC). Protein was supplemented with ammonium sulfate until a final concentration of 1.4 M was reached. The protein solution was filtered and loaded onto an HIC column at 4 ml/min in Buffer A2: 25 mM Tris pH 7.5, 1 mM EDTA, 1.4 M $(NH_4)_2SO_4$, 1 mM DTT. Protein was eluted with a gradient of 0–100% Buffer B over 30 minutes (Buffer B2: 25 mM Tris pH 7.5, 1 mM EDTA, 1 mM DTT, 1% glycerol). Finally, the purified protein was dialyzed at 4° C. into the appropriate assay buffer (25 mM Tris pH 8, 100 mM NaCl, 5 mM EDTA, 1 mM DTT, 1% glycerol). Yields varied from mutant to mutant but typically were within the range of 3–20 mg/L culture.

EXAMPLE 3

This example describes one illustrative method for determining the $IC_{50}$ of the compounds of the present invention against PTP-1B. Substrate, pNPP (Sigma), was dissolved at 4 mM in 1×HN buffer (50 mM HEPES pH 7.0; 100 mM NaCl; 1 mM DTT) and 83 ul was mixed with 2 ul DMSO or 2 ul compound in DMSO. The reaction was started by addition of PTP-1B (750 ηg in standard assay conditions) in 15 μl 1×HN buffer. The rate of product formation (OD405 nm minus OD655 nm, BioRad Benchmark or Molecular Devices Spectramax 190) was measured every 30 seconds for 15 minutes at 25 degrees C, and data were analyzed by linear regression. For endpoint assays, the reaction was stopped after 15 min. with 50 μl 3M NaOH and OD405 nm-OD655 nm was measured. For $IC_{50}$ determination, rates normalized relative to uninhibited controls were plotted against compound concentration and fitted using a 4 parameter non-linear regression curve fit ($y=[(A-D)/(1+\{x/C\}^B)]+D$, Spectramax Software package).

EXAMPLE 4

This example describes some of the methods that were used to validate that the compounds of the present invention bind to PTP-1B at the exosite region.

Figure 8:
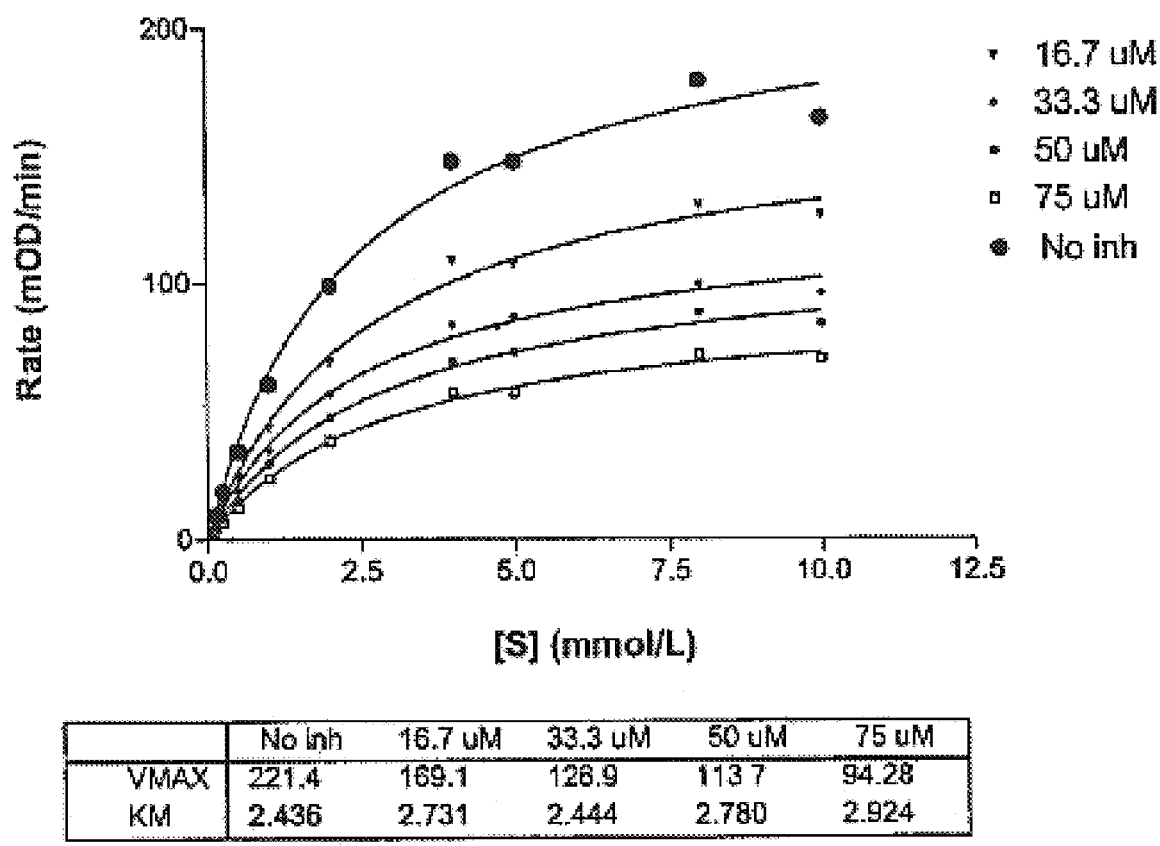
FIG. 8 is a plot of the reaction velocity of PTP-1B versus increasing concentration of substrate in the presence of varying concentrations of compound 5.

The compounds of the present invention, typified by compound 5 ($IC_{50}$=30 μM), behave as if PTP-1B had an allosteric site. When the reaction velocity is plotted against substrate concentration (PNPP) in the presence of varying concentrations of compound 5, a sigmoidal dependence is shown instead of the hyperbolic plot predicted by Michaelis-Menton. Moreover, as typical with allosteric inhibitors and as shown by FIG. 8, there is a decrease in $V_{max}$ with increasing inhibitor concentration but with no significant effect on $K_m$.

To the assess whether the truncation of PTP-1B affected the results, enzymatic studies were performed on both the 298 residue version and the 403 amino acid version which only lacks the terminal hydrophobic 35 amino acids. Both forms of PTP-1B showed similar results although the potency of the exosite inhibitors against the 403 amino acid form of PTP-1B tended to be slightly more potent.

To assess whether the inhibition of PTP-1B with the exosite compounds were due to some artifact such as the formation of a covalent complex, protein denaturation, aggregation or precipitation, a time dependence experiment was performed. Increasing incubation time from 5 minutes to over an hour had no impact on inhibition. Direct binding kinetics showed a fast on-rate and a relatively fast off-rate. In addition, biacore data showed that compound 5 bound to PTP-1B with a 1:1 binding stoichiometry. This was further substantiated by a protein titration experiment in which the concentration of PTP-1B was increased from 210 nM to 21 μM by addition of catalytically inactive PTP-1B mutations (C215S or D181C versions of SEQ ID NO. 1). In the presence of 21 μM of PTP-1B mutants, the $IC_{50}$ of compound 5 was determined to be 77 μM and 81 μM respectively, which was consistent with the $IC_{50}$ using IR peptide substrate (71 μM) and the biacore $K_d$ (75 μM). In addition, a crystal structure of PTP-1B bound to compound 5 was solved showing the compound 5 bound to the exosite region.

EXAMPLE 5

Figure 9:
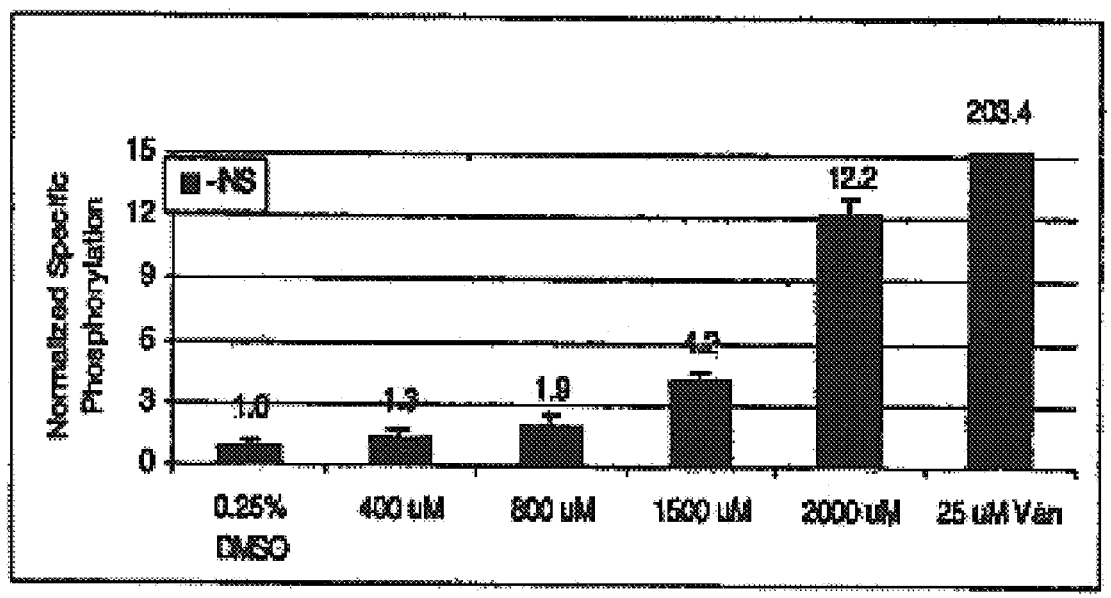
FIG. 9 is a dose response curve for insulin receptor phosphorylation as a function of increasing concentration of compound 5.

This example describes an illustrative assay for quantifying the degree of insulin receptor phosphorylation in cells. Any suitable cells can be used. In this example, CHO-IR cells were grown in DMEM w/10% fetal bovine serum supplemented with penicillin and streptomycin. Cells were plated at a density of 40,000 cells per well in a 96 well plate. The following day, the medium was changed to DMEM without serum and the cells were serum starved for 16 hours. 1 hour prior to harvesting, varying concentrations of a test compound diluted in DMEM were added to the cells. Where indicated, human insulin was added to cells 10 minutes prior to harvesting. Cell were lysed in 30 mM HEPES, 150 mM NaCl, 1% triton X-100, and 0.02% sodium azide. Insulin receptor phosphorylation was quantitated in an ELISA assay as described previously (Jongsoon Lee). FIG. 9 shows the dose response curve for compound 5. As it can be seen, the level of insulin receptor phosphorylation is a function of the concentration of compound 5.

EXAMPLE 6

Figure 10:
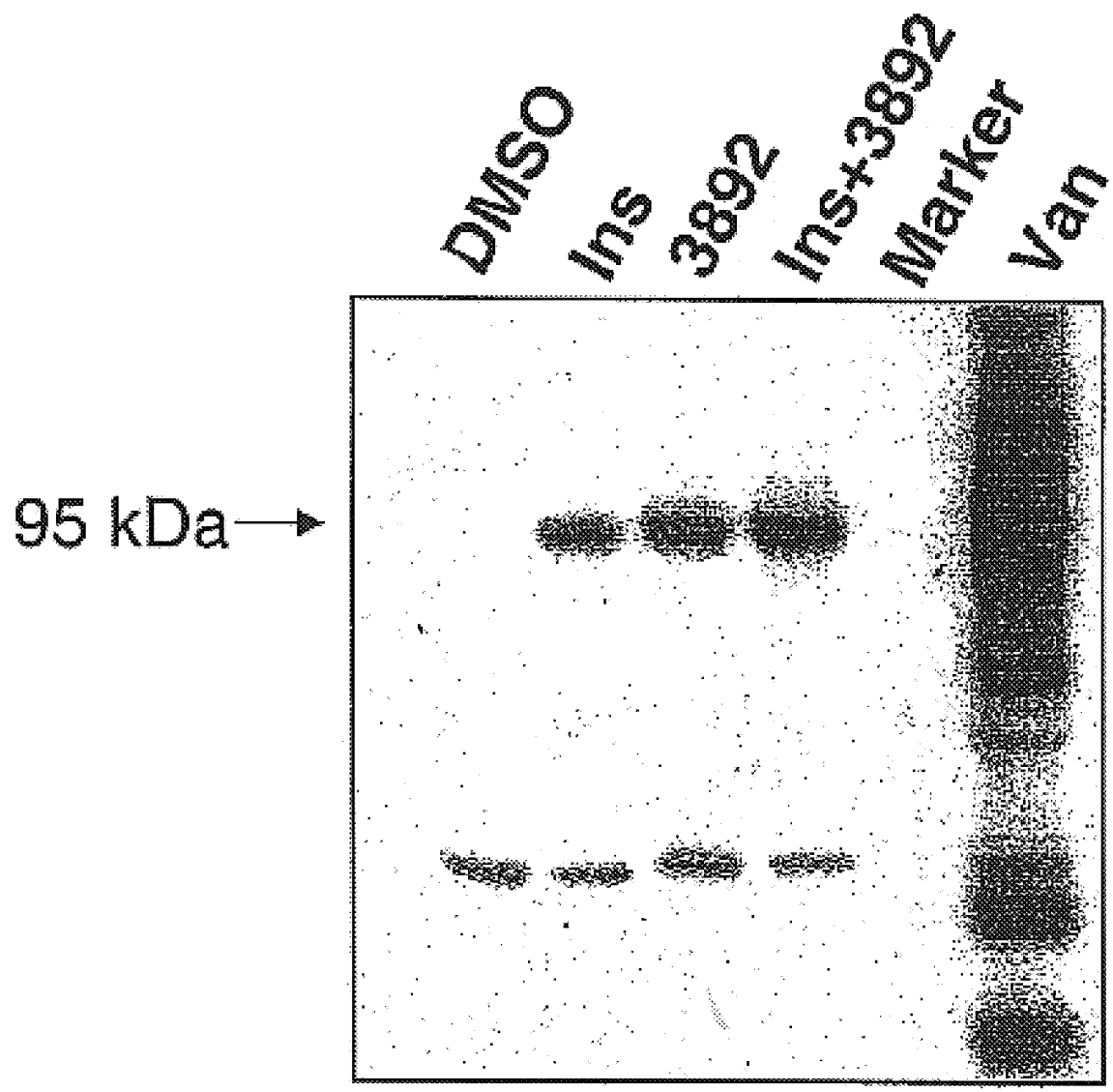
FIG. 10 is a Western blot showing the selectivity of compound 5 in cells. The 95 kDa band corresponds to the insulin receptor. DMSO is the negative control and vanadate (the lane marked "Van"), a nonspecific phosphatase inhibitor, is the positive control.

This example describes a typical western blot experiment to assess the specificity of the compounds of the present invention to inhibit PTP-1B as opposed to other phosphatases. In this example, CHO-IR cells were used. CHO-IR cells were grown in complete medium as stated above in the cell-based assay. Cells were then plated at a density of 300,000 cells per well in a 6-well plate. The following day cells were serum starved for 16 hours. One hour prior to lysis, cells were treated with either DMSO, 2 mM SP3892, or 25 uM pervanadate. Ten minutes prior to lysis, 1 uM human insulin was added to the wells indicated. Cells were lysed with the same buffer stated above in the cell-based assay with the addition of 0.1% SDS. Following lysis, total cell lysate was loaded onto a 4–12% Bis-Tris gel, and proteins were then transferred onto a PVDF membrane. The membrane was blocked in 5% milk/TBST for 1 hour at room temperature and then incubated with an anti-IR/IGF-1R [pYpY1162/1163] primary antibody overnight. The following day, the membrane was washed in TBST and incubated with a goat-anti-rabbit secondary antibody for 1 hour at room temperature followed by ECL development. FIG. 10 shows a western blot for compound 5. The 95 kDa band corresponds to the insulin receptor. DMSO is the negative control; vanadate (the lane marked "Van"), a nonspecific phosphatase inhibitor, is the positive control; "3892" corresponds to compound 5; and "Ins" corresponds to insulin.

EXAMPLE 7

This example describes additional screening methods for potential exosite inhibitors. These assays are used to distinguish between true exosite inhibitors from those compounds that inhibit through some non-specific interaction.

In one method, a candidate for an exosite inhibitor is tested using a range of enzyme concentrations that is capable of allosteric regulation (referred herein as the catalytically competent enzyme). If the compound is inhibiting solely through the allosteric mechanism, then the observed inhibition should be predictable. For example, the fraction of saturable inhibition or the theoretical inhibition of an enzyme can be calculated as follows:

$$f=[Ki+E(tot)+I(tot)-sqrt(((Ki+E(tot)+I(tot))^2)-4*E(tot)*I(tot))]/(2*E(tot))$$

where:

f is the fraction saturable inhibition;

Ki is the inhibition constant or $IC_{50}$;

E(tot) is the concentration of catalytically competent enzyme; and

I(tot) is the inhibitor concentration.

For example, if $IC_{50}$ of an allosteric inhibitor is 3 μM, the inhibitor concentration is 3 μM, and the concentration of catalytically competent enzyme is 0.01 μM, then the theoretical inhibition is 49.94%. If the concentration of catalytically competent enzyme is increased to 1.29 μM, under the same conditions, then the theoretical inhibition is 44.69%. Thus, if the candidate for an exosite inhibitor is a true allosteric inhibitor, than increasing the enzyme concentration from 0.01 μM to 1.29 μM will not result in a significant change in the observed inhibition. Thus, if a dramatic change were observed when the enzyme concentration is varied from 0.01 μM and 1.29 μM, than the candidate compound is not an exosite inhibitor but is likely to be inhibiting the enzyme through a non-specific interaction.

In another method, the non-specific interaction is eliminated by assaying the candidate compound against the same concentration of enzyme that is capable of allosteric regulation but in the presence of increasing concentrations of inactivated enzyme, typically between 0.25 and 1 times the putative $IC_{50}$ of the candidate exosite inhibitor. For example, an inactivated PTP-1B or TC-PCP is one that is no longer capable of dephosphorylating a tyrosine. In this manner, the expected inhibition for an exosite inhibitor remains constant despite the increasing overall protein concentration. An illustrative example of an inactivated PTP-1B and TC-PCP is where the active site cysteine (Cys215) of each respective phosphatase is mutated to a serine. Other methods for eliminating compounds that inhibit in a non-specific manner also can be used such as those described by McGovern et al., *J. Med. Chem.*, 45: 1712–1722 (2002) which is incorporated herein by reference.

EXAMPLE 8

This example describes the synthesis of the following compound

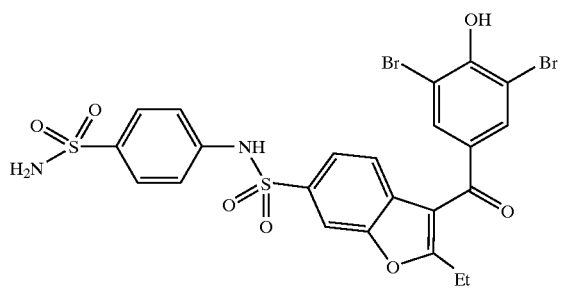

which was prepared according to Scheme A and the protocol below.

SCHEME A

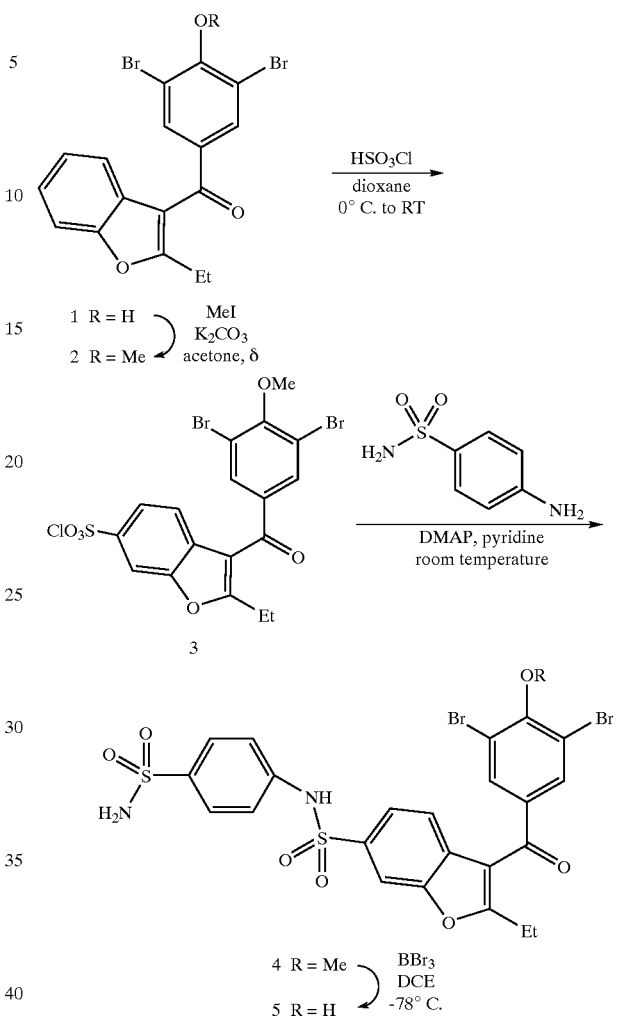

Compound 1. Benzbromarone (compound 1) was purchase from the Sigma-Aldrich chemical company.

Compound 2. A heterogeneous mixture of 1 (26.8 g, 60.0 mmol), $K_2CO_3$ (33.5 g, 240 mmol), and methyl iodide (12.9 g, 90.0 mmol) in acetone (200 mL) was heated to reflux for 16 hours. Ethyl acetate (300 mL) was added, and the mixture was extracted sequentially with water (200 mL), 2.5 M NaOH (2×100 mL), and brine (100 mL). The organic portion was dried over $Na_2SO_4$ and concentrated to give 26.3 g (100% yield) of the title compound as a white solid. $^1$H NMR ($CDCl_3$): δ1.36 (t, J=7.5 Hz, 3 H), 2.90 (q, J=7.5 Hz, 2 H), 3.98 (s, 3 H), 7.24 (app t, J=7.4 Hz, 1 H), 7.32 (app t, J=7.2 Hz, 1 H), 7.42 (d, J=7.2 Hz, 1 H), 7.50 (d, J=7.9 Hz, 1 H), 7.99 (s, 2 H). LRMS: ion 438 (M+).

Compound 3. A clear, pale yellow solution of 2 (5.28 g, 12.0 mmol) in anhydrous dioxane (12 mL) was cooled to 0° C. and treated dropwise with neat chlorosulfonic acid (42.4 g, 360 mmol) over two hours with vigorous mixing. The reaction mixture was carefully transferred dropwise into a rapidly stirred slurry of 1 M HCl (200 mL) and crushed ice (600 mL). The cloudy mixture was extracted with ether (2×300 mL). The combined organic extracts were dried over $Na_2SO_4$ and concentrated to give a viscous oil. Flash column chromatography (96:4 hexane/ethyl acetate) afforded 3.10 g (48% yield) of the title compound as a white solid. $^1$H NMR ($CDCl_3$): δ1.41 (t, J=7.4 Hz, 3 H), 2.95 (q, J=7.4 Hz, 2 H), 4.00 (s, 3 H), 7.70 (d, J=8.5 Hz, 1 H), 7.96 (d, J=8.5 Hz, 1 H), 7.97 (s, 2 H), 8.22 (s, 1 H). LRMS: ion 536 (M+).

Compound 4. To a stirring mixture of 4-amino benzenesulfonamide (0.25 g, 1.45 mmoL), anhydrous pyridine (0.3 mL, 3.80 mmoL) and DMAP ("dimethylaminopyridine") (0.006 g, 0.049 mmoL) in 10 mL of anhydrous THF ("tetrahydrofuran") was added 6-chlorosulfonyl benzbromarone methyl ether (compound 3) (0.5 g, 0.938 mmoL) in 5 mL of THF via syringe dropwise. After stirred at room temperature for 6 h, the reaction mixture was diluted with ethyl acetate (200 mL). The organic layer was washed with 1.0 N HCl aq. solution (2×60 mL) and brine, dried over. $Na_2SO_4$, and concentrated under reduced pressure. The crude product was purified on a silica gel flash column (10–20% EtOAc in Hexane as eluent) to give 0.412 g (0.615 mmoL, 65.6%) as a light yellow solid.

Compound 5. To a stirring solution of compound 4 in 15 mL of anhydrous DCE at −78° C. was added 1.0 M $BBr_3$ in DCM (3.1 mL, 3.08 mmoL) slowly. After completion of addition, the resulting mixture was allowed warm up to room temperature and stir for 4 h. The reaction was quenched with 1.0 N HCl aq. solution. The reaction mixture was extracted with DCM (2×100 mL), the combined organic layer was washed with brine, dried over $Na_2SO_4$, concentrated under reduced pressure. The residue was purified on preparative HPLC to give 0.192 g (0.293 mmoL, 47.6%) as a white solid. $^1$H NMR (DMSO-$d_6$, 400 MHz) δ8.03 (s, 1H), δ7.89 (s, 2H), δ7.71 (d, J=8.61, 3H), δ7.53 (d, J=8.37, 1H), δ7.26 (d, J=8.67, 2H), δ2.85 (q, J=7.52, 2H), δ1.31 (t, J=7.50, 3H); MS (API-ES+) at m/z 656, 658, 660.

EXAMPLE 9

This example describes the synthesis of compounds of the structure

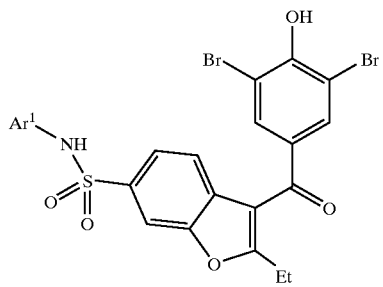

where Et is ethyl and $Ar^1$ is unsubstituted aryl or substituted aryl (where the term aryl includes heteroaryl). These compounds were made according to Example 8 except that $Ar^1NH_2$ was used instead of 4-amino-benzenesulfonamide. Illustrative examples of specific embodiments of $Ar^1NH_2$ and their resulting products are shown in Table 1.

TABLE 1

TABLE 1-continued
| Ar¹NH₂ | Product |
|---|---|
| | |
| | |
| | |
| | |
EXAMPLE 10
This example describes the synthesis of the following compound
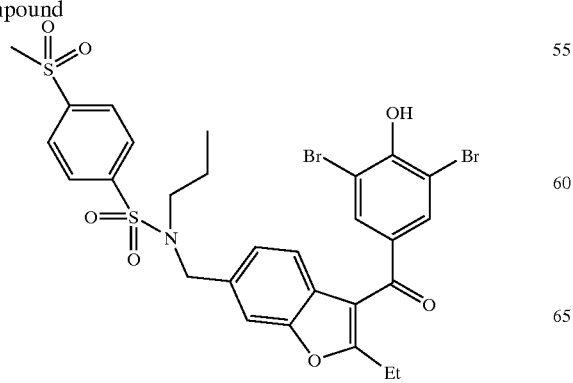

which was made according to Scheme B and the protocol below.

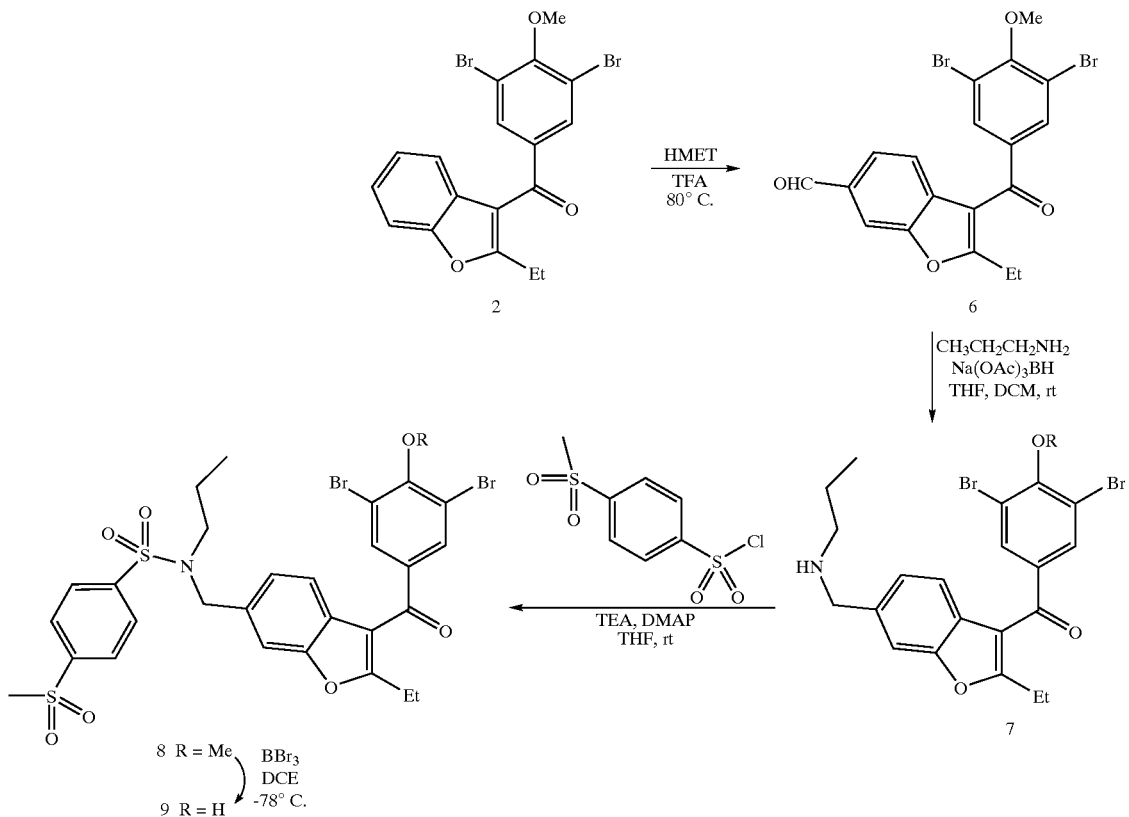

SCHEME B

Compound 6. To a mixture of benzbromarone methyl ether (0.3 g, 0.696 mmol) and hexamethylenetetramine ("HMET") (0.483 g, 3.45 mmoL) was added slowly 20 mL of TFA ("trifluoracetic acid"). The reaction mixture was heated at 80° C. for 48 hours. The reaction mixture was cooled to room temperature, pooled to 60 mL of ice-water, and strongly stirred. The mixture was extracted with EtoAc (3×80 mL), and the combined organic solution was washed with water and brine, dried over Na$_2$SO$_4$, filtered and concentrated. Flash chromatography over silica gel (10% ethyl acetate in hexanes) provided the desired aldehyde as light yellow oil (0.180 g, 55.7%). $^1$H NMR (CDCl$_3$, 400 MHz) δ10.2 (s, 1H), δ7.98 (s, 1H), δ7.94 (s, 2H), δ7.76 (d, (d, J=8.13 Hz, 1H), δ7.54 (d, J=8.09 Hz, 1H), δ3.94 (s, 3H), δ2.92 (q, J=7.50, 7.52, 7.52 Hz, 2H), δ1.35 (t, J=7.50, 7.52 Hz, 3H); MS (API-ES$^+$) at m/z 463, 465, 467.

Compound 7. Compound 6 (0.100 g, 0.216 mmol) was dissolved in THF/DCM (1:1). Propylamine (0.047 mL, 0.648 mmol) was added, followed by addition of catalytic amount of concentrated acetic acid. After stirring for 5 minutes, the sodium triacetoxyboronhydride (0.090 g, 0.432 mmol) was added in one portion at room temperature. The reaction mixture was stirred for 2 hours and then the solvent portion of the reaction mixture was removed under reduced pressure. The residue was partitioned between 50 mL of EtOAc and 50 mL of saturated NaHCO$_3$ aqueous solution. The aqueous solution was extracted with EtOAc (2×30 mL), and the combined organic solution was washed with brine, dried over Na$_2$SO$_4$, filtered, concentrated. The crude product was used for next step without purification. $^1$H NMR, (DMSO-d$_6$, 400 MHz) δ8.00 (s, 2H), δ7.80(s, 1H), δ7.45 (d, J=8.13 Hz, 1H), δ7.38 (d, J=8.09 Hz, 1H δ4.25 (s, 2H), δ3.89 (s, 3H), δ2.87 (m, 4H), δ1.62 (m, 2H), δ1.25 (t, J=7.47, 7.40 Hz, 3H), δ0.87 (t, J=7.48, 7.45 Hz, 3H); MS (API-ES$^+$) at m/z 508, 510, 512.

Compound 8. To a stirring mixture of compound 7 (0.050 g, 0.0986 mmoL), triethylamine (0.110 mL, 0.788 mmoL), and DMAP (0.006 g, 0.049 mmoL) in 2 mL of anhydrous THF was added dropwise by syringe 4-methanesulfonyl-benzenesulfonyl chloride (0.075 g, 0.295 mmoL) in 1 mL of THF. After stirring at room temperature for 3 hours, the reaction mixture was diluted with EtOAc (30 mL). The organic solution was washed with 1.0 N HCl aqueous solution (1×20 mL), water and brine, dried over Na$_2$SO$_4$, and concentrated. The crude product was purified on a silica gel flash column (20% EtOAc in Hexane) to give 0.061 g (0.083 mmoL, 81.1%) as a light yellow solid. MS (API-ES$^+$) at m/z 725, 727, 729.

Compound 9. To a stirring solution of compound 8 (0.061 g, 0.083 mmol) in 5 mL of anhydrous DCE at −78° C. was added slowly 1.0 M BBr$_3$ in DCM (0.250 mL, 0.250 mmoL). The resulting mixture was allowed to warm up to room temperature and was stirred for 4 hours. The reaction was quenched with 1.0 N HCl aqueous solution. The resulting reaction mixture was extracted with DCM (2×30 mL), and the combined organic solution was washed with brine, dried over Na$_2$SO$_4$, and concentrated. The residue was purified on preparative HPLC to give 0.030 g (0.043 mmoL, 51.8%) as a white solid. $^1$H NMR (DMSO-d$_6$, 400 MHz) d 8.13 (s, 4H), δ7.91 (s, 2H), δ7.60 (s, 1H), δ7.45 (d, J=8.13 Hz, 1H), δ7.25 (d, J=8.09 Hz, 1H), δ4.50 (s, 2H), δ3.55 (s, 3H), δ3.18 (m, 2H), δ2.75 (m, 2H), δ1.25 (m, 5H), δ0.63 (t, J=7.27, 7.36 Hz, 3H); MS (API-ES$^+$) at m/z 713, 715, 717.

EXAMPLE 11

This example describes the synthesis of compounds of the structure

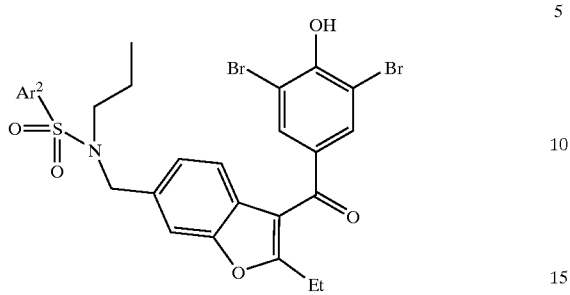

where Et is ethyl and $Ar^2$ is unsubstituted aryl or substituted aryl (where the term aryl includes heteroaryl). These compounds were made according to Example 10 except that $Ar^2SO_2Cl$ was used instead of 4-methanesulfonyl-benzenesulfonyl chloride. Illustrative examples of specific embodiments of $Ar^2SO_2Cl$ and their resulting products are shown in Table 2.

TABLE 2

| $Ar^2SO_2Cl$ | Product |
|---|---|

All references cited throughout the specification are hereby expressly incorporated herein by reference.

While the present invention has been described with reference to the specific embodiments thereof, it would be understood by those skilled in the art that various changes may be made and equivalents may be substituted without departing from the true spirit and scope of the invention. In addition, many modifications may be made to adapt a particular situation, material, composition of matter, process, process step or steps, to the objection, spirit and scope of the present invention. All such modifications are intended to be within the scope of the claims appended hereto.

What is claimed is:

1. A compound having the structure

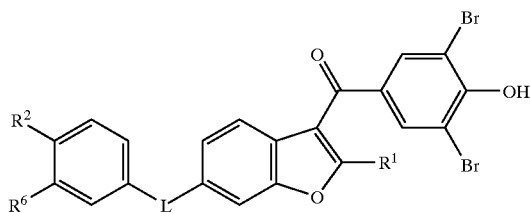

wherein:

$R^1$ is hydrogen, methyl, ethyl, propyl;

$R^2$ is hydrogen, —S(O$_2$)R$^3$, —NHC(=O)R$^3$, —NHC(=O)CH$_2$(C=O)OR$^3$, —S(O$_2$)NR$^4$R$^5$, or —NR$_4$S(O$_2$)R$^3$ where R$^3$ is C$_1$–C$_5$ alkyl, R$^4$ is hydrogen, C$_4$–C$_5$ alkyl, unsubstituted cyclic moiety, or substituted cyclic moiety, and R$^5$ is either hydrogen or R$^5$ and R$^4$ together form an unsubstituted cyclic moiety or a substituted cyclic moiety;

$R^6$ is hydrogen or alternatively when R$^2$ as —NR$^4$S(O$_2$)NR$^3$, then R$^6$ and R$^4$ together form an unsubstituted cyclic moiety or substituted cyclic moiety; and, L is —NHS(O$_2$)— or —S(O$_2$)NR$^7$CH$_2$— where R$^7$ is hydrogen or C$_4$–C$_5$ alkyl.

2. The compound of claim 1 wherein the one or more substituents on the substituted cyclo group axe each independently selected from the group consisting of: C$_1$–C$_5$ alkyl, phenyl, benzyl, F, Cl, I, Br, —OH, —NO$_2$; —CN; —CF$_3$; —CH$_2$CF$_3$; —CH$_2$Cl; —CH$_2$OH; —CH$_2$CH$_2$OH; —CH$_2$NH$_2$; —CH$_2$SO$_2$CH$_3$; —OR$^8$; —C(O)R$^8$; —COOR$^{88}$; —C(O)NR$^8$R$^9$; —OC(O)R$^8$; —OCOOR$^8$; —OC(O)NR$^8$R$^9$; —NR$^8$R$^9$; —S(O)$_2$R$^8$; and —NR$^8$C(O)R$^9$ where R$^8$ and R$^9$ are each independently hydrogen, C$_4$–C$_5$ alkyl, phenyl or benzyl.

3. The compound of claim 1 wherein R$^2$ and R$^6$ are both hydrogen.

4. The compound of claim 1 wherein R$^2$ is —S(O$_2$)NHR$^5$ where R$^5$ is an unsubstituted cyclic moiety or substituted cyclic moiety, and R$^6$ is hydrogen.

5. The compound of claim 1 wherein R$^2$ is —S(O$_2$)R$^3$ where R$^3$ is methyl, ethyl, or propyl, and R$^6$ is hydrogen.

6. The compound of claim 1 wherein R$^2$ is —NHC(=O)R$^3$ where R$^3$ is methyl, ethyl, or propyl, and R$^6$ is hydrogen.

7. The compound of claim 1 wherein R$^2$ is —NHC(=O)CH$_2$(C=O)OR$^3$ where R$^3$ is methyl, ethyl, or propyl, and R$^6$ is hydrogen.

8. The compound of claim 1 wherein R$^2$ is —NR$^4$S(O$_2$)R$^3$ wherein R$^3$ is methyl and R$^4$ and R$^6$ together form an unsubstituted heterocyclo or a substituted heterocyclo.

9. A compound having the structure

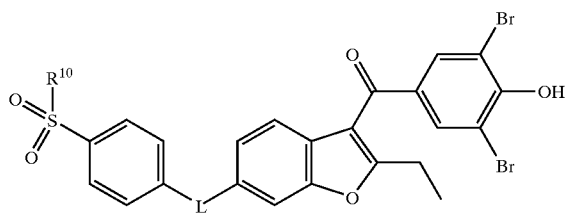

wherein:
R$^{10}$ is C$_4$–C$_5$ alkyl or NHR$^{11}$ where R$^{11}$ is hydrogen, C$_1$–C$_{10}$ alkyl or aryl and,
L is —NHS(O$_2$)— or —S(O$_2$)NH(CH$_2$)$_3$CH$_2$—.

10. The compound of claim 9 wherein R$^{10}$ is methyl, ethyl or propyl.

11. The compound of claim 9 wherein R$^{10}$ is NHR$^{11}$ and R$^{11}$ is hydrogen.

12. The compound of claim 9 wherein R$^{10}$ is NHR$^{11}$ and R$^{11}$ is aryl.

13. The compound of claim 9 wherein R$^1$1 is phenyl.

14. The compound of claim 9 wherein R$^{11}$ is heteroaryl.

15. An exosite mutant of PTP-1B.

16. An exosite mutant of TC-PTP.

17. A pharmaceutical composition comprising an effective amount of a compound of claim 1 or 9, or a prodrug or pharmaceutically acceptable derivative thereof, in admixture with a pharmaceutically acceptable carrier.

18. A method of identifying an exosite inhibitor of PTP-1B comprising
   a) contacting a test compound with PTP-1B;
   b) contacting the test compound with an exosite mutant of PTP-1B; and
   c) comparing the activity of PTP-1B in the presence of the test compound with the activity of the exosite mutant of PTP-1B in the presence of the test compound.

19. A method of identifying an exosite inhibitor of TC-PTP comprising
   a) contacting a test compound with TC-PTP;
   b) contacting the test compound with an exosite mutant of TC-PTP; and
   c) comparing the activity of TC-PTP in the presence of the test compound with the activity of the exosite mutant of TC-PTP in the presence of the test compound.

20. A method for treating type 2 diabetes, or a pathologic condition associated with type 2 diabetes, comprising administering to a subject in need thereof a therapeutically effective amount of a PTP-1B exosite inhibitor of claim 1.

21. The method of claim 20 wherein the pathologic condition associated with type 2 diabetes is insulin resistance.

22. A method for treating inflammation is provided comprising administering to a subject in need thereof a therapeutically effective amount of a TC-PTP exosite inhibitor of claim 1.

23. A method for treating an immune system disorder comprising administering to a subject in need thereof a therapeutically effective amount of a TC-PTP exosite inhibitor of claim 1.

24. A method for treating a hematopoiesis disorder comprising administering to a subject in need thereof a therapeutically effective amount of a TC-PTP exosite inhibitor of claim 1.

* * * * *

SEQUENCE LISTING

<160> NUMBER OF SEQ ID NOS: 29

<210> SEQ ID NO 1
<211> LENGTH: 298
<212> TYPE: PRT
<213> ORGANISM: Homo sapiens

<400> SEQUENCE: 1

Met Glu Met Glu Lys Glu Phe Glu Gln Ile Asp Lys Ser Gly Ser Trp
 1               5                  10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val His Cys Ser Ala Gly Ile Gly Arg Ser Gly Thr
    210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
        275                 280                 285

Asp Gln Trp Lys Glu Leu Ser His Glu Asp
    290                 295

<210> SEQ ID NO 2
<211> LENGTH: 296
<212> TYPE: PRT
<213> ORGANISM: Homo sapiens

<400> SEQUENCE: 2

Met Pro Thr Thr Ile Glu Arg Glu Phe Glu Glu Leu Asp Thr Gln Arg
 1               5                  10                  15

-continued

```
Arg Trp Gln Pro Leu Tyr Leu Glu Ile Arg Asn Glu Ser His Asp Tyr
             20                  25                  30

Pro His Arg Val Ala Lys Phe Pro Glu Asn Arg Asn Arg Asn Arg Tyr
             35                  40                  45

Arg Asp Val Ser Pro Tyr Asp His Ser Arg Val Lys Leu Gln Asn Ala
 50                  55                  60

Glu Asn Asp Tyr Ile Asn Ala Ser Leu Val Asp Ile Glu Glu Ala Gln
 65                  70                  75                  80

Arg Ser Tyr Ile Leu Thr Gln Gly Pro Leu Pro Asn Thr Cys Cys His
                 85                  90                  95

Phe Trp Leu Met Val Trp Gln Gln Lys Thr Lys Ala Val Val Met Leu
             100                 105                 110

Asn Arg Ile Val Glu Lys Glu Ser Val Lys Cys Ala Gln Tyr Trp Pro
             115                 120                 125

Thr Asp Asp Gln Glu Met Leu Phe Lys Glu Thr Gly Phe Ser Val Lys
 130                 135                 140

Leu Leu Ser Glu Asp Val Lys Ser Tyr Tyr Thr Val His Leu Leu Gln
145                 150                 155                 160

Leu Glu Asn Ile Asn Ser Gly Glu Thr Arg Thr Ile Ser His Phe His
                 165                 170                 175

Tyr Thr Thr Trp Pro Asp Phe Gly Val Pro Glu Ser Pro Ala Ser Phe
             180                 185                 190

Leu Asn Phe Leu Phe Lys Val Arg Glu Ser Gly Ser Leu Asn Pro Asp
             195                 200                 205

His Gly Pro Ala Val Ile His Cys Ser Ala Gly Ile Gly Arg Ser Gly
 210                 215                 220

Thr Phe Ser Leu Val Asp Thr Cys Leu Val Leu Met Glu Lys Gly Asp
225                 230                 235                 240

Asp Ile Asn Ile Lys Gln Val Leu Leu Asn Met Arg Lys Tyr Arg Met
                 245                 250                 255

Gly Leu Ile Gln Thr Pro Asp Gln Leu Arg Phe Ser Tyr Met Ala Ile
             260                 265                 270

Ile Glu Gly Ala Lys Cys Ile Lys Gly Asp Ser Ser Ile Gln Lys Arg
             275                 280                 285

Trp Lys Glu Leu Ser Lys Glu Asp
 290                 295

<210> SEQ ID NO 3
<211> LENGTH: 296
<212> TYPE: PRT
<213> ORGANISM: Homo sapiens

<400> SEQUENCE: 3

Pro Ile Thr Asp Leu Ala Asp Asn Ile Glu Arg Leu Lys Ala Asn Asp
 1               5                  10                  15

Gly Leu Lys Phe Ser Gln Glu Tyr Glu Ser Ile Asp Pro Gly Gln Gln
             20                  25                  30

Phe Thr Trp Glu Asn Ser Asn Leu Glu Val Asn Lys Pro Lys Asn Arg
             35                  40                  45

Tyr Ala Asn Val Ile Ala Tyr Asp His Ser Arg Val Ile Leu Thr Ser
 50                  55                  60

Ile Asp Gly Val Pro Gly Ser Asp Tyr Ile Asn Ala Asn Tyr Ile Asp
 65                  70                  75                  80

Gly Tyr Arg Lys Gln Asn Ala Tyr Ile Ala Thr Gln Gly Pro Leu Pro
```

-continued

```
                    85                  90                  95
Glu Thr Met Gly Asp Phe Trp Arg Met Val Trp Glu Gln Arg Thr Ala
                100                 105                 110
Thr Val Val Met Met Thr Arg Leu Glu Glu Lys Ser Arg Val Lys Cys
            115                 120                 125
Asp Gln Tyr Trp Pro Ala Arg Gly Thr Glu Thr Cys Gly Leu Ile Gln
        130                 135                 140
Val Thr Leu Leu Asp Thr Val Glu Leu Ala Thr Tyr Thr Val Arg Thr
145                 150                 155                 160
Phe Ala Leu His Lys Ser Gly Ser Glu Lys Arg Glu Leu Arg Gln
                165                 170                 175
Phe Gln Phe Met Ala Trp Pro Asp His Gly Val Pro Glu Tyr Pro Thr
                180                 185                 190
Pro Ile Leu Ala Phe Leu Arg Arg Val Lys Ala Cys Asn Pro Leu Asp
            195                 200                 205
Ala Gly Pro Met Val Val His Cys Ser Ala Gly Val Gly Arg Thr Gly
        210                 215                 220
Cys Phe Ile Val Ile Asp Ala Met Leu Glu Arg Met Lys His Glu Lys
225                 230                 235                 240
Thr Val Asp Ile Tyr Gly His Val Thr Cys Met Arg Ser Gln Arg Asn
                245                 250                 255
Tyr Met Val Gln Thr Glu Asp Gln Tyr Val Phe Ile His Glu Ala Leu
                260                 265                 270
Leu Glu Ala Ala Thr Cys Gly His Thr Glu Val Pro Ala Arg Asn Leu
            275                 280                 285
Tyr Ala His Ile Gln Lys Leu Gly
        290                 295

<210> SEQ ID NO 4
<211> LENGTH: 320
<212> TYPE: PRT
<213> ORGANISM: Homo sapiens

<400> SEQUENCE: 4

Met Glu Met Glu Lys Glu Phe Glu Gln Ile Asp Lys Ser Gly Ser Trp
1               5                  10                  15
Ala Ala Ile Tyr Gln Asp Ile Arg His Glu Ala Ser Asp Phe Pro Cys
            20                  25                  30
Arg Val Ala Lys Leu Pro Lys Asn Lys Asn Arg Asn Arg Tyr Arg Asp
        35                  40                  45
Val Ser Pro Phe Asp His Ser Arg Ile Lys Leu His Gln Glu Asp Asn
    50                  55                  60
Asp Tyr Ile Asn Ala Ser Leu Ile Lys Met Glu Glu Ala Gln Arg Ser
65                  70                  75                  80
Tyr Ile Leu Thr Gln Gly Pro Leu Pro Asn Thr Cys Gly His Phe Trp
                85                  90                  95
Glu Met Val Trp Glu Gln Lys Ser Arg Gly Val Val Met Leu Asn Arg
                100                 105                 110
Val Met Glu Lys Gly Ser Leu Lys Cys Ala Gln Tyr Trp Pro Gln Lys
            115                 120                 125
Glu Glu Lys Glu Met Ile Phe Glu Asp Thr Asn Leu Lys Leu Thr Leu
        130                 135                 140
Ile Ser Glu Asp Ile Lys Ser Tyr Tyr Thr Val Arg Gln Leu Glu Leu
145                 150                 155                 160
```

```
Glu Asn Leu Thr Thr Gln Glu Thr Arg Glu Ile Leu His Phe His Tyr
                165                 170                 175
Thr Thr Trp Pro Asp Phe Gly Val Pro Glu Ser Pro Ala Ser Phe Leu
            180                 185                 190
Asn Phe Leu Phe Lys Val Arg Glu Ser Gly Ser Leu Ser Pro Glu His
                195                 200                 205
Gly Pro Val Val His Cys Ser Ala Gly Ile Gly Arg Ser Gly Thr
210                 215                 220
Phe Cys Leu Ala Asp Thr Cys Leu Leu Leu Met Asp Lys Arg Lys Asp
225                 230                 235                 240
Pro Ser Ser Val Asp Ile Lys Lys Val Leu Leu Glu Met Arg Lys Phe
                245                 250                 255
Arg Met Gly Leu Ile Gln Thr Ala Asp Gln Leu Arg Phe Ser Tyr Leu
            260                 265                 270
Ala Val Ile Glu Gly Ala Lys Phe Ile Met Gly Asp Ser Ser Val Gln
                275                 280                 285
Asp Gln Trp Lys Glu Leu Ser His Glu Asp Leu Glu Pro Pro Pro Glu
            290                 295                 300
His Ile Pro Pro Pro Arg Pro Pro Lys Arg Ile Leu Glu Pro His
305                 310                 315                 320

<210> SEQ ID NO 5
<211> LENGTH: 29
<212> TYPE: DNA
<213> ORGANISM: Homo sapiens

<400> SEQUENCE: 5
gccatatgga gatggaaaag gagttcgag                                      29

<210> SEQ ID NO 6
<211> LENGTH: 40
<212> TYPE: DNA
<213> ORGANISM: Homo sapiens

<400> SEQUENCE: 6
gcgacgcgaa ttcttaattg tgtggctcca ggattcgttt                          40

<210> SEQ ID NO 7
<211> LENGTH: 34
<212> TYPE: DNA
<213> ORGANISM: Homo sapiens

<400> SEQUENCE: 7
tgccggaatt ccttagtcct cgtgggaaag ctcc                                34

<210> SEQ ID NO 8
<211> LENGTH: 27
<212> TYPE: DNA
<213> ORGANISM: Homo sapiens

<400> SEQUENCE: 8
ttcttggcgt tcttcgcaa agtccga                                         27

<210> SEQ ID NO 9
<211> LENGTH: 27
<212> TYPE: DNA
<213> ORGANISM: Homo sapiens

<400> SEQUENCE: 9
gactttgcga agaaacgcca agaatga                                        27
```

```
<210> SEQ ID NO 10
<211> LENGTH: 21
<212> TYPE: DNA
<213> ORGANISM: Homo sapiens

<400> SEQUENCE: 10
ggtgccaaat gcatcatggg g                                              21

<210> SEQ ID NO 11
<211> LENGTH: 21
<212> TYPE: DNA
<213> ORGANISM: Homo sapiens

<400> SEQUENCE: 11
ccccatgatg catttggcac c                                              21

<210> SEQ ID NO 12
<211> LENGTH: 34
<212> TYPE: DNA
<213> ORGANISM: Homo sapiens

<400> SEQUENCE: 12
tgccggaatt ccttagtcct cgtgcgaaag ctcc                                34

<210> SEQ ID NO 13
<211> LENGTH: 31
<212> TYPE: DNA
<213> ORGANISM: Homo sapiens

<400> SEQUENCE: 13
gaatgaggct ggtgagcaag ggactccaaa g                                   31

<210> SEQ ID NO 14
<211> LENGTH: 27
<212> TYPE: DNA
<213> ORGANISM: Homo sapiens

<400> SEQUENCE: 14
gaatgaggct gggcattcag ggactcc                                        27

<210> SEQ ID NO 15
<211> LENGTH: 27
<212> TYPE: DNA
<213> ORGANISM: Homo sapiens

<400> SEQUENCE: 15
gttcaagaat gagcatggtg attcagg                                        27

<210> SEQ ID NO 16
<211> LENGTH: 29
<212> TYPE: DNA
<213> ORGANISM: Homo sapiens

<400> SEQUENCE: 16
ctgactctcg gacgcagaaa agaaagttc                                      29

<210> SEQ ID NO 17
<211> LENGTH: 30
<212> TYPE: DNA
<213> ORGANISM: Homo sapiens

<400> SEQUENCE: 17
```

```
gagtgaccct gagcatcgga ctttgaaaag                                    30

<210> SEQ ID NO 18
<211> LENGTH: 27
<212> TYPE: DNA
<213> ORGANISM: Homo sapiens

<400> SEQUENCE: 18
gatgcctgca ctggagtgca ccacaac                                        27

<210> SEQ ID NO 19
<211> LENGTH: 27
<212> TYPE: DNA
<213> ORGANISM: Homo sapiens

<400> SEQUENCE: 19
ctggatcagc ccacaccgaa acttcct                                        27

<210> SEQ ID NO 20
<211> LENGTH: 27
<212> TYPE: DNA
<213> ORGANISM: Homo sapiens

<400> SEQUENCE: 20
ctggtcggct gtacagatca gccccat                                        27

<210> SEQ ID NO 21
<211> LENGTH: 28
<212> TYPE: DNA
<213> ORGANISM: Homo sapiens

<400> SEQUENCE: 21
cttcgatcac agcgcagtag gagaagcg                                       28

<210> SEQ ID NO 22
<211> LENGTH: 27
<212> TYPE: DNA
<213> ORGANISM: Homo sapiens

<400> SEQUENCE: 22
gaatttggca ccgcagatca cagccag                                        27

<210> SEQ ID NO 23
<211> LENGTH: 27
<212> TYPE: DNA
<213> ORGANISM: Homo sapiens

<400> SEQUENCE: 23
agagtccccc atgcagaatt tggcacc                                        27

<210> SEQ ID NO 24
<211> LENGTH: 27
<212> TYPE: DNA
<213> ORGANISM: Homo sapiens

<400> SEQUENCE: 24
ccactgatcc tggcaggaag agtcccc                                        27

<210> SEQ ID NO 25
<211> LENGTH: 27
<212> TYPE: DNA
<213> ORGANISM: Homo sapiens

<400> SEQUENCE: 25
```

```
ccaaaagtga ccggctgtgt taggcaa                                    27

<210> SEQ ID NO 26
<211> LENGTH: 27
<212> TYPE: DNA
<213> ORGANISM: Homo sapiens

<400> SEQUENCE: 26
ccagtattgt gcggctttta acgaacc                                    27

<210> SEQ ID NO 27
<211> LENGTH: 27
<212> TYPE: DNA
<213> ORGANISM: Homo sapiens

<400> SEQUENCE: 27
ccagtattgt gcgcttttta acgaacc                                    27

<210> SEQ ID NO 28
<211> LENGTH: 17
<212> TYPE: DNA
<213> ORGANISM: Homo sapiens

<400> SEQUENCE: 28
aatacgactc actatag                                               17

<210> SEQ ID NO 29
<211> LENGTH: 20
<212> TYPE: DNA
<213> ORGANISM: Homo sapiens

<400> SEQUENCE: 29
tagttattgc tcagcggtgg                                            20
```